US012653780B2

(12) United States Patent (10) Patent No.: US 12,653,780 B2
Paiement et al. (45) Date of Patent: Jun. 16, 2026

(54) METHOD OF TREATMENT AND DEVICE FOR THE IMPROVED BIOAVAILABILITY OF LEUKOTRIENE RECEPTOR ANTAGONISTS

(71) Applicant: INTELGENX CORP., Saint-Laurent (CA)

(72) Inventors: Nadine Paiement, St-Laurent (CA); Horst G. Zerbe, Hudson (CA); Justin W. Conway, Carignan (CA); Rodolphe Obeid, St-Laurent (CA); Ludwig Aigner, Freilassing (DE); Johanna Michael, Salzburg (AT)

( * ) Notice: Subject to any disclaimer, the term of this patent is extended or adjusted under 35 U.S.C. 154(b) by 170 days.

(21) Appl. No.: 17/732,456

(22) Filed: Apr. 28, 2022

(65) Prior Publication Data

US 2022/0395452 A1 Dec. 15, 2022

Related U.S. Application Data

(63) Continuation of application No. 16/131,995, filed on Sep. 14, 2018, now abandoned, which is a continuation-in-part of application No. 15/940,288, filed on Mar. 29, 2018, now abandoned, and a continuation-in-part of application No. 15/067,309, filed on Mar. 11, 2016, now abandoned, and a continuation-in-part of application No. 15/299,054, filed on Oct. 20, 2016, now Pat. No. 9,949,934.

(60) Provisional application No. 62/478,876, filed on Mar. 30, 2017.

(51) Int. Cl.
| | |
|---|---|
| *A61K 9/00* | (2006.01) |
| *A61K 31/47* | (2006.01) |
| *A61K 47/02* | (2006.01) |
| *A61K 47/10* | (2017.01) |
| *A61K 47/12* | (2006.01) |
| *A61K 47/18* | (2017.01) |
| *A61K 47/26* | (2006.01) |
| *A61K 47/36* | (2006.01) |
| *A61K 47/38* | (2006.01) |

(52) U.S. Cl.
CPC ............ *A61K 9/006* (2013.01); *A61K 9/0056* (2013.01); *A61K 31/47* (2013.01); *A61K 47/02* (2013.01); *A61K 47/10* (2013.01); *A61K 47/12* (2013.01); *A61K 47/18* (2013.01); *A61K 47/183* (2013.01); *A61K 47/26* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,695,463 | A | 9/1987 | Yang et al. |
| 6,660,292 | B2 | 12/2003 | Zerbe et al. |
| 7,132,113 | B2 | 11/2006 | Zerbe et al. |
| 7,674,479 | B2 | 3/2010 | Zerbe et al. |
| 8,575,194 | B1 | 11/2013 | Schultz |
| 8,691,272 | B2 | 4/2014 | Zerbe et al. |
| 8,703,191 | B2 | 4/2014 | Zerbe et al. |
| 8,735,374 | B2 | 5/2014 | Zerbe et al. |
| 9,149,472 | B2 | 10/2015 | Schultz |
| 9,301,948 | B2 | 4/2016 | Zerbe et al. |
| 9,539,334 | B2 | 1/2017 | Wood et al. |
| 9,668,970 | B2 | 6/2017 | Obeid et al. |
| 9,717,682 | B2 | 8/2017 | Zerbe et al. |
| 9,949,934 | B1 | 4/2018 | Zerbe et al. |
| 10,272,038 | B2 | 4/2019 | Obeid et al. |
| 10,610,528 | B2 | 4/2020 | Zerbe et al. |
| 10,722,476 | B2 | 7/2020 | Zerbe et al. |
| 10,828,254 | B2 | 11/2020 | Paiement et al. |
| 11,033,493 | B2 | 6/2021 | Obeid et al. |
| 11,471,406 | B2 | 10/2022 | Paiement et al. |
| 11,602,504 | B2 | 3/2023 | Madwar et al. |

(Continued)

FOREIGN PATENT DOCUMENTS

| | | |
|---|---|---|
| CA | 3017526 A1 | 3/2020 |
| CN | 106176685 A | 12/2016 |

(Continued)

OTHER PUBLICATIONS

Baliga, S., et al., J Indian Soc Periodontol, 17(4): 461-465 (2013). (Year: 2013).*

Khatoon, N., et al., International Journal of Pharmaceutical Sciences and Research, 5: 1780-1787 (2014). (Year: 2014).*

"Gum arabic", From Wikipedia, the free encyclopedia. [online] Retrieved from "http://en.wikipedia.org/w/index.php?title=Gum_arabic&oldid=767071650". Feb. 23, 2017.

Morepen, The Joy of Growing Together, [online] Retrieved from "http://www.morepen.com/api-product-information.htm". (2010). (The year of publication is sufficiently earlier than the effective U.S. filing date so that the particular month of publication is not an issue).

(Continued)

*Primary Examiner* — David J Blanchard
*Assistant Examiner* — Daniel F Coughlin
(74) *Attorney, Agent, or Firm* — Anglehart et al.

(57) ABSTRACT

Disclosed is a method of administration and device for the improved bioavailability of leukotriene receptor antagonists. This method and device involve an alkaline surface pH oral film dosage form designed to deliver leukotriene receptor antagonists, such as Montelukast, to the stomach in an amorphous precipitate suspended in aqueous medium. Also disclosed is a device and method for treating a disease, such as a neurodegenerative disease or condition associated with neuroinflammation induced by a leukotriene. The device is a film unit dosage form having an alkaline surface pH film layer and a safe and effective amount of Montelukast. The device is configured and formulated to predominantly achieve enteral delivery of the Montelukast. The method includes enterally delivering to a human or an animal in need of treatment, a safe and effective amount of Montelukast capable of crossing the blood-brain barrier.

19 Claims, 17 Drawing Sheets

(56) References Cited

U.S. PATENT DOCUMENTS

| | | | |
|---|---|---|---|
| 11,648,212 | B2 | 5/2023 | Bilal et al. |
| 2004/0131661 | A1 | 7/2004 | Auffret |
| 2004/0156794 | A1 | 8/2004 | Barkalow et al. |
| 2005/0107426 | A1 | 5/2005 | Overeem et al. |
| 2007/0053939 | A1 | 3/2007 | Yokoyama |
| 2007/0190139 | A1 | 8/2007 | Zerbe et al. |
| 2009/0214640 | A1 | 8/2009 | Szabo et al. |
| 2010/0297232 | A1 | 11/2010 | Myers et al. |
| 2011/0136815 | A1 | 6/2011 | Zerbe et al. |
| 2011/0142889 | A1 | 6/2011 | Lee et al. |
| 2011/0263606 | A1 | 10/2011 | Zerbe et al. |
| 2012/0141585 | A1 | 6/2012 | Coulter |
| 2012/0156229 | A1 | 6/2012 | Park et al. |
| 2013/0039932 | A1 | 2/2013 | Park et al. |
| 2013/0177605 | A1 | 7/2013 | Asari et al. |
| 2014/0065217 | A1 | 3/2014 | Zerbe et al. |
| 2014/0155483 | A1 | 6/2014 | Li et al. |
| 2016/0022595 | A1 | 1/2016 | Shikani et al. |
| 2016/0051510 | A1 | 2/2016 | Allen |
| 2016/0074396 | A1 | 3/2016 | Jeon |
| 2016/0175245 | A1 | 6/2016 | Brewer et al. |
| 2016/0220480 | A1 | 8/2016 | Bilal et al. |
| 2016/0229845 | A1 | 8/2016 | Cao et al. |
| 2016/0243036 | A1 | 8/2016 | Paiement et al. |
| 2016/0324773 | A1 | 11/2016 | Paiement et al. |
| 2017/0216220 | A1 | 8/2017 | Bilal et al. |
| 2017/0258710 | A1 | 9/2017 | Conway et al. |
| 2017/0290807 | A1 | 10/2017 | Mundada |
| 2017/0290870 | A1 | 10/2017 | Schaneville |
| 2017/0304319 | A1 | 10/2017 | Westrin |
| 2018/0078549 | A1 | 3/2018 | Zerbe et al. |
| 2018/0110724 | A1 | 4/2018 | Zerbe et al. |
| 2018/0250240 | A1 | 9/2018 | Paiement et al. |
| 2019/0133925 | A1 | 5/2019 | Paiement et al. |
| 2019/0209459 | A1 | 7/2019 | Obeid et al. |
| 2019/0231685 | A1 | 8/2019 | Paiement et al. |
| 2019/0247505 | A1 | 8/2019 | Paiement et al. |
| 2019/0290595 | A1 | 9/2019 | Zerbe et al. |
| 2019/0314293 | A1 | 10/2019 | Bilal et al. |
| 2020/0138885 | A1 | 5/2020 | Paiement et al. |
| 2020/0215063 | A1 | 7/2020 | Zerbe et al. |
| 2021/0015738 | A1 | 1/2021 | LaRosa |
| 2021/0393611 | A1 | 12/2021 | Madwar et al. |
| 2022/0362164 | A1 | 11/2022 | Paiement et al. |
| 2022/0409584 | A1 | 12/2022 | Bilal et al. |
| 2023/0047314 | A1 | 2/2023 | Paiement et al. |
| 2023/0201130 | A1 | 6/2023 | Madwar et al. |
| 2023/0225965 | A1 | 7/2023 | Tir et al. |
| 2023/0248660 | A1 | 8/2023 | Bilal et al. |

FOREIGN PATENT DOCUMENTS

| | | | |
|---|---|---|---|
| EP | 0743064 | A1 | 11/1996 |
| WO | 9940898 | | 8/1999 |
| WO | 2008038155 | A2 | 4/2008 |
| WO | 2010/107404 | A1 | 9/2010 |
| WO | 2012121461 | A1 | 9/2012 |
| WO | 2013107810 | A1 | 7/2013 |
| WO | 2016134454 | A1 | 9/2016 |
| WO | 2018176149 | A1 | 10/2018 |
| WO | 2018205017 | A1 | 11/2018 |
| WO | 2020051709 | A1 | 3/2020 |
| WO | 2022165607 | A1 | 8/2022 |
| WO | 2022170442 | A1 | 8/2022 |

OTHER PUBLICATIONS

Okumu et al., "Dynamic Dissolution Testing to Establish In Vitro/In Vivo Correlations for Montelukast Sodium, a Poorly Soluble Drug", Pharmaceutical Reasearch, vol. 25, No. 12, Dec. 2008.

Raghavendra Rao N. G et al., "Development of Mucoadhesive Films for Buccal Administration of Montelukast", IJPT, Mar. 2010, vol. 2, Issue No. 1, 1-15.

Hughes, L. "Ion exchange resinates—the technology behind the mystery" 2005, Pharmaceutical Technology Europe, 17(4), 38-42.

Hallucinogens: LSD, Peyote, Psilocybin, and PCP. National Institute on Drug Abuse (2008).

The Dow Chemical Company, 2002 (Year: 2002).

López-Olaondo et al. (British Journal of Anaesthesia, 1996, 76, 835-840).

Balakrishnan, P., et al. Enhanced oral bioavailability of Coenzyme Q10 by self-emulsifying drug delivery systems. International Journal of Pharmaceutics, (2009), 374(1-2), 66-72.

English Translation of WO2012121461A1, published Sep. 13, 2012. Machine Translation.

Vishvakarma, "Design and development of montelukast sodium fast dissolving films for better therapeutic efficacy", Journal of the Chilean Chemical Society, 63(2), pp. 3988-3993, Jun. 1, 2018 (Jun. 1, 2018).

Eleftheriadis, Georgios K. et al. Unidirectional drug release from 3D printed mucoadhesive buccal films using FDM technology: In vitro and ex vivo evaluation. European Journal of Pharmaceutics and Biopharmaceutics 144 (2019) 180-192.

Vieira, E. et al., Evaluation of Brewer's spent yeast to produce flavor enhancer nucleotides: influence of serial repitching. Aug. 20, 2013, Journal of Agricultural and Food Chemistry, vol. 61, 8724-8729.

Arthur Okumu, et al., Dynamic Dissolution Testing to Establish In Vitro/In Vivo Correlations for Montelukast Sodium, a Poorly Soluble Drug. Pharmaceutical Research. Published: Jun. 17, 2008. vol. 25, pp. 2778-2785, (2008).

Corresponding U.S. Appl. No. 17/729,442 final rejection mailed Apr. 21, 2025.

* cited by examiner

○ = Tablet particle containing API

Oral Trans-Mucosal Absorption

Enteric Absorption

◯ = Solubilized Film particle containing API

⬡ = Solubilized Film or Tablet particle containing API

Figure 5

| | A Vehicle Tg female | A Vehicle Tg male | B 3 mg/kg/day Tg female | B 3 mg/kg/day Tg male | C 10 mg/kg/day Tg female | C 10 mg/kg/day Tg male |
|---|---|---|---|---|---|---|
| Number of values | 7 | 8 | 7 | 7 | 8 | 7 |

METHOD OF TREATMENT AND DEVICE FOR THE IMPROVED BIOAVAILABILITY OF LEUKOTRIENE RECEPTOR ANTAGONISTS

CROSS-REFERENCE TO RELATED APPLICATIONS

This application is a continuation of U.S. application Ser. No. 16/131,995, filed on Sep. 14, 2018, that is a continuation-in-part of U.S. application Ser. No. 15/940,288, filed Mar. 29, 2018, and which claims priority to Provisional Application No. 62/478,876, filed Mar. 30, 2017, and which also is a continuation-in-part of U.S. application Ser. No. 15/067,309, filed Mar. 11, 2016; and Ser. No. 15/299,054, filed Oct. 20, 2016 (now U.S. Pat. No. 9,949,934). These documents are hereby incorporated by reference in their entireties.

FIELD OF THE DISCLOSURE

This disclosure concerns a formulation and method of treatment and pharmaceutical dosage form for improving the bioavailability of a leukotriene receptor antagonist or leukotriene synthesis inhibitor for the treatment of a disorder.

BACKGROUND OF THE DISCLOSURE

As the brain ages, it loses its ability to generate new cells, while existing cells lose functionality, including the ability to prevent inflammatory mediators in the blood from passing through the blood-brain bather (BBB). At the same time the aged brain tends to produce higher levels of inflammatory agents such as leukotrienes, and loses some of its ability to counter the effects of inflammatory mediators, resulting in neuroinflammation and cognitive impairment. A major contributor to neuroinflammation are leukotrienes. There is evidence that leukotriene receptor antagonists, such as Montelukast sodium, have the potential to reduce neuroinflammation and restore brain cell function. Such treatments can be effective for treating various neurodegenerative diseases and conditions, including Huntington's disease, Parkinson's disease, loss of memory function, spinal cord and brain injuries, and stroke.

Montelukast (MTL) sodium is an orally active leukotriene receptor antagonist commonly used to treat patients suffering from chronic asthma as well as symptomatic relief of seasonal allergic rhinitis. During a normal respiratory inflammation response, the binding of cysteinyl leukotrienes to the leukotriene receptor induces inflammation within the respiratory pathway, generating asthmatic symptoms. MTL functions to suppress this inflammatory response by binding to the leukotriene receptor with high affinity and selectivity, thereby blocking the pathway leading to the physiological response for extended periods. Recently, neuroinflammation within the brain has been linked to age-related dementia and neurodegenerative diseases. MTL applied under these biological conditions has been shown to significantly reduce neuroinflammation, elevate hippocampal neurogenesis and improve learning and memory in old animals.

Presently, Montelukast sodium is marketed in a tablet form under the name of "Singulair®." One of the greatest challenges for using MTL in a tablet form is the inconsistent bioavailability. Although MTL is freely soluble in water, its solubility is reduced under acidic conditions normally found in the stomach. This has led to relatively slow and inconsistent absorption into the blood stream, with maximum concentrations occurring only after 2-4 hours, thereby limiting its use to chronic applications rather than for rapid acute treatment. Experimental studies indicate that the major obstacles limiting MTL absorption pertain to its solubility, the rate of dissolution from the tablet platform and the rate of transport/permeation across biological membranes.

U.S. Pat. Nos. 8,575,194 and 9,149,472 disclose methods of improving cognitive impairments by administering Montelukast in a single tablet or capsule that comprises an extended release (ER) component and an immediate release (IR) component in a single dosage unit. The method involves administering the dosage unit to provide an initial burst of IR active pharmaceutical ingredient (API) into the system, followed by the ER API over the course of 12 hours, thereby maintaining a constant effective plasma level. Disclosed embodiments include a tablet with an ER core and an IR shell or a capsule containing a mixture of ER and IR beads combined in a specific ratio to achieve the desired effect. In an alternative embodiment, the regimen in general consists of an initial high dose of 10 mg of MTL followed by 5 mg doses approximately every 2 hours afterwards over the course of 12 hours. The patents discuss plasma levels as being critical for achieving cognitive improvement.

However, MTL can only exert its therapeutic effects if it crosses the blood-brain barrier (BBB) and accumulates in the cerebrospinal fluid (CSF) at sufficient concentration levels. Neither plasma nor CSF concentration levels of MTL are discussed in the patents.

Moreover, pharmacokinetics research related to MTL CSF concentrations indicates (see page 7 pharmacokinetics research document) that MTL is not expected to cross the BBB as it is more than 99% bound to plasma proteins. In this study rats dosed with radiolabeled MTL exhibited only minimal distribution across the blood-brain barrier.

Surge Dose® Montelukast tablets have been proposed in a method for improving the formulation of a tablet capable of accelerated API release. The method attempts to improve MTL solubility in the stomach. The Surge Dose® product may still be limited by gastric emptying cycles and food effects similar to the Singulair® tablet and chewable. The chewable tablet is also comprised of solid MTL.

There is thus a need for method of treatment that overcome the shortcomings of the prior art.

SUMMARY OF THE DISCLOSURE

Disclosed is an alkaline oral film dosage form for improving bioavailability of leukotriene antagonist inhibitor. Accordingly, the oral film dosage form deliver leukotriene antagonist inhibitor such as Montelukast in a form that renders it suitable for improved bioavailability when compared with commercially available oral dosage forms. The disclosed oral film dosage form has an alkaline surface pH that is preferably greater than to 7.5, more preferably greater than to 8.5 and optimally greater than to 9.

Disclosed is an alkaline oral film dosage form comprising from 10 to 70 mg of Montelukast.

Disclosed is a method of treating the symptoms

Disclosed is a dosage form of a leukotriene receptor antagonist exhibiting an improved bioavailability as compared with existing oral dosage forms.

Disclosed is an exemplary dosage form exhibiting an improved bioavailability of Montelukast leukotriene receptor antagonist.

Disclosed is a dosage form for delivering to the brain a safe and effective amount of leukotriene receptor antagonists for reducing neuroinflammation.

soluilizedDisclosed is an exemplary dosage form for delivering to the brain a safe and effective amount of Montelukast for reducing neuroinflammation.

Disclosed is a pharmaceutical dosage form for human pharmaceutical use, comprising Montelukast salt, free base, or prodrug in a unit dosage form suitable for oral administration. The dosage form can be configured for enteral delivery of the active agent. The Montelukast salt, free base, or prodrug according to the disclosed dosage form can be configured to reach the stomach in an amorphous form in aqueous suspension.

Disclosed is Montelukast solubilized in an oral dosage form. The oral dosage form is orally administered such as on the tongue, buccaly or sublingually. Upon contact of the dosage form with saliva, the dosage form preferably solubilizes and/or disintegrates. The dissolution and/or disintegration of the oral dosage form transforms the solubilized Montelukast into a suspended and/or insoluble precipitate creating a pre-solubilized dosage form ready to be absorbed and/or swallowed in the oral cavity.

According to an aspect of the present disclosure, the pre-solubilized dosage form improves the bioavailability of the Montelukast compared with the equivalent tablet or chewable oral dosage forms.

The Montelukast may be delivered through the use of a film layer having an alkaline surface pH. As such, Montelukast salt, free base, or prodrug is disposed within or on a polymeric film suitable for oral administration. The films can be formulated for rapid disintegration and distribution of micro- or nano-scopic particles of the active agent in the gastrointestinal tract.

In certain embodiments, the active agent in the film dosage form is Montelukast sodium.

According to an aspect of the present disclosure, there is provided an alkaline surface pH Montelukast oral film dosage form having an improved bioavailability when compared to swallowable and chewable oral tablet dosage forms.

Also disclosed is a method of treating conditions where leukotriene inhibition is desired (achieved through blockage of the receptor of synthesis of leukotriene themselves), which comprises administering to a patient in need thereof an oral film dosage form having an alkaline surface pH containing about 10 to about 75 mg of Montelukast, as needed, up to a total dose of 75 mg per day for the treatment of neuroinflammation, for a period of no less than 30 continuous days, preferably 60 continuous days, and most preferably 90 continuous days.

Specific conditions that can be treated by the present disclosure, include, but are not limited to, neuroinflammation, neurodegenerative diseases and cognitive impairment.

The unit dosage form is suitable for oral administration to treat neuroinflammation. The unit dosage form contains about 10 mg to about 70 mg, preferably between about 20 mg to about 60 mg and most preferably between about 30 mg to about 50 mg of the compound and is administered once or twice per day.

Also disclosed is a method of treating a neurodegenerative disease or neuroinflammatory disorder. The method comprising the steps of enterally delivering to a person or other animal in need of treatment for a neurodegenerative disease or neuroinflammatory disorder via a film dosage form, a safe and effective amount of a leukotriene receptor antagonist, wherein the amount of Montelukast is about 10 mg to about 70 mg per day, preferably between about 20 mg to about 60 mg and most preferably between about 30 mg to about 50 mg and wherein leukotriene receptor antagonist is enterally delivered as a precipitate suspended in an aqueous medium, wherein the precipitate is generated orally upon dissolution and/or disintegration of an oral film dosage form Also disclosed is an oral film dosage form, comprising: a film layer having an alkaline surface pH; and a safe and effective amount of a leukotriene receptor antagonist incorporated into the film layer. The film layer is formulated to dissolve and/or disintegrate when in contact with an aqueous solution. The leukotriene receptor antagonist is preferably incorporated into the film layer in an amorphous form and most preferably solubilized in the film layer. A preferred film dosage form comprises Montelukast, present in an amount of about 10 mg to about 70 mg, preferably between about 20 mg to about 60 mg and most preferably between about 30 mg to about 50 mg.

Also disclosed is an oral film dosage form having a film layer with an alkaline surface pH; and a safe and effective amount of a leukotriene receptor antagonist incorporated into the film layer wherein the film layer dissolves and/or disintegrates in contact with an aqueous solution. The alkaline surface pH is preferably greater than pH 7.5, more preferably greater than pH 8.5 and optimally greater than pH 9. Also disclosed is an oral dosage form having an unbuffered alkaline surface pH.

Also disclosed is a film dosage form comprising Montelukast, wherein the area under the curve (AUC) is between about 3120 and about 4700 ng*h/mL and/or wherein the Cmax is between about 475 and about 720 ng/mL.

Also disclosed is a method of treating neurodegenerative diseases and conditions at least partially induced by leukotrienes, by administering to a person or other animal in need of treatment, a film dosage form including a film layer comprising Montelukast. The film layer(s) is configured for enteral delivery of the active agent.

The film layer may also be configured for transmucosal or sublingual delivery.

These and other features, advantages and objects of the various embodiments will be better understood with reference to the following specification and claims.

BRIEF DESCRIPTION OF THE DRAWINGS

FIG. 5 is a graphical representation of the dissolution data shown in table 12.

DETAILED DESCRIPTION OF ILLUSTRATIVE EMBODIMENTS

Figure 1:
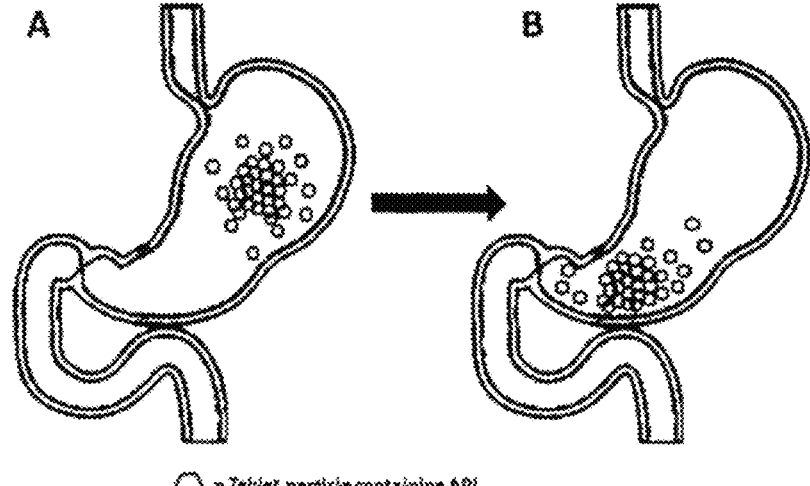
FIG. 1 is a representation of the dissolution of swallowable tablets.

In accordance with certain aspects of this disclosure, methods of administration and devices for the improved bioavailability of leukotriene inhibitors are provided. These methods and devices involve an oral dosage form designed to deliver leukotriene inhibitors such as Montelukast, to the mouth and stomach in the form of an amorphous precipitate suspended in an aqueous medium (e.g., saliva and/or gastric fluids).

In accordance with certain aspects of this disclosure, methods for treating neurodegenerative diseases and/or other conditions that are at least partially induced by leukotrienes are provided. These methods include enteral delivery or a combination of transmucosal, sublingual or both transmucosal and sublingual, along with enteral delivery of Montelukast. The Montelukast is incorporated into a film layer in an amount that is safe and effective to reduce leukotriene induced neuroinflammation in patients.

Neurodegenerative diseases that can be treated in accordance with this disclosure include, but are not limited to, loss of memory function (long term or short term), dementia, apathy, depression, fatigue (acute or chronic), cognitive losses, loss of focus, loss of libido, and disorientation. Specific disease conditions that can be treated with the disclosed methods include Huntington's disease, Parkinson's disease and Alzheimer's disease. Such treatments can also be effective for treating neurological diseases, neurodegenerative diseases, neuroinflammatory disorders, traumatic or posttraumatic disorders, vascular or more precisely, neurovascular disorders, hypoxic disorders, and postinfectious central nervous system disorders. The term "neurodegenerative disease" or "neurological disease" or "neuroinflammatory disorder" refers to any disease, disorder, or condition affecting the central or peripheral nervous system, including ADHD, AIDS-neurological complications, absence of the Septum Pellucidum, acquired epileptiform aphasia, acute disseminated encephalomyelitis, adrenoleukodystrophy, agenesis of the Corpus Callosum, agnosia, Aicardi Syndrome, Alexander Disease, Alpers' Disease, alternating hemiplegia, Alzheimer's Disease, amyotrophic lateral sclerosis (ALS), anencephaly, aneurysm, Angelman Syndrome, angiomatosis, anoxia, aphasia, apraxia, arachnoid cysts, arachnoiditis, Arnold-Chiari Malformation, arteriovenous malformation, aspartame, Asperger Syndrome, ataxia telangiectasia, ataxia, attention deficit-hyperactivity disorder, autism, autonomic dysfunction, back pain, Barth Syndrome, Batten Disease, Behcet's Disease, Bell's Palsy, benign essential blepharospasm, benign focal amyotrophy, benign intracranial hypertension, Bernhardt-Roth Syndrome, Binswanger's Disease, blepharospasm, Bloch-Sulzberger Syndrome, brachial plexus birth injuries, brachial plexus injuries, Bradbury-Eggleston Syndrome, brain aneurysm, brain injury, brain and spinal tumors, Brown-Sequard Syndrome, bulbospinal muscular atrophy, Canavan Disease, Carpal Tunnel Syndrome, causalgia, cavernomas, cavernous angioma, cavernous malformation, central cervical cord syndrome, central cord syndrome, central pain syndrome, cephalic disorders, cerebellar degeneration, cerebellar hypoplasia, cerebral aneurysm, cerebral arteriosclerosis, cerebral atrophy, cerebral beriberi, cerebral gigantism, cerebral hypoxia, cerebral palsy, cerebro-oculo-facio-skeletal syndrome, Charcot-Marie-Tooth Disorder, Chiari Malformation, chorea, choreoacanthocytosis, chronic inflammatory demyelinating polyneuropathy (CIDP), chronic orthostatic intolerance, chronic pain, Cockayne Syndrome Type II, Coffin Lowry Syndrome, coma, including persistent vegetative state, complex regional pain syndrome, congenital facial diplegia, congenital myasthenia, congenital myopathy, congenital vascular cavernous malformations, corticobasal degeneration, cranial arteritis, craniosynostosis, Creutzfeldt-Jakob Disease, cumulative trauma disorders, Cushing's Syndrome, cytomegalic inclusion body disease (CIBD), cytomegalovirus infection, dancing eyes-dancing feet syndrome, Dandy-Walker Syndrome, Dawson Disease, De Morsier's Syndrome, Dejerine-Klumpke Palsy, delir in elderly, trauma-induced delir, dementia-multi-infarct, dementia-subcortical, dementia with Lewy Bodies, dermatomyositis, developmental dyspraxia, Devic's Syndrome, diabetic neuropathy, diffuse sclerosis, Dravet's Syndrome, dysautonomia, dysgraphia, dyslexia, dysphagia, dyspraxia, dystonias, early infantile epileptic encephalopathy, Empty Sella Syndrome, encephalitis lethargica, encephalitis and meningitis, encephaloceles, encephalopathy, encephalotrigeminal angiomatosis, epilepsy, Erb's Palsy, Erb-Duchenne and Dejerine-Klumpke Palsies, Fabry's Disease, Fahr's Syndrome, fainting, familial dysautonomia, familial hemangioma, familial idiopathic basal ganglia calcification, familial spastic paralysis, febrile seizures (e.g., GEFS and GEFS plus), Fisher Syndrome, Floppy Infant Syndrome, Friedreich's Ataxia, Gaucher's Disease, Gerstmann's Syndrome, Gerstmann-Straussler-Scheinker Disease, giant cell arteritis, giant cell inclusion disease, globoid cell leukodystrophy, glossopharyngeal neuralgia, Guillain-Barre Syndrome, HTLV-1 associated myelopathy, Hallervorden-Spatz Disease, head injury, headache, hemicrania continua, hemifacial spasm, hemiplegia alterans, hereditary neuropathies, hereditary spastic paraplegia, heredopathia atactica polyneuritiformis, Herpes Zoster Oticus, Herpes Zoster, Hirayama Syndrome, holoprosencephaly, Huntington's Disease, hydranencephaly, hydrocephalus-normal pressure, hydrocephalus, hydromyelia, hypercortisolism, hypersomnia, hypertonia, hypotonia, hypoxia, immune-mediated encephalomyelitis, inclusion body myositis, incontinentia pigmenti, infantile hypotonia, infantile phytanic acid storage disease, infantile refsum disease, infantile spasms, inflammatory myopathy, intestinal lipodystrophy, intracranial cysts, intracranial hypertension, Isaac's Syndrome, Joubert Syndrome, Kearns-Sayre Syndrome, Kennedy's Disease, Kinsbourne syndrome, Kleine-Levin syndrome, Klippel Feil Syndrome, Klippel-Trenaunay Syndrome (KTS), Kliver-Bucy Syndrome, Korsakoffs Amnesic Syndrome, Krabbe Disease, Kugelberg-Welander Disease, kuru, Lambert-Eaton Myasthenic Syndrome, Landau-Kleffner Syndrome, lateral femoral cutaneous nerve entrapment, lateral medullary syndrome, learning disabilities, Leigh's Disease, Lennox-Gastaut Syndrome, Lesch-Nyhan Syndrome, leukodystrophy, Levine-Critchley Syndrome, Lewy Body Dementia, lissencephaly, locked-in syndrome, Lou Gehrig's Disease, lupus-neurological sequelae, Lyme Disease-Neurological Complications, Machado-Joseph Disease, macrencephaly, megalencephaly, Melkersson-Rosenthal Syndrome, meningitis, Menkes Disease, meralgia paresthetica, metachromatic leukodystrophy, microcephaly, migraine, Miller Fisher Syndrome, mini-strokes, mitochondrial myopathies, Mobius Syndrome, monomelic amyotrophy, motor neuron diseases, Moyamoya Disease, mucolipidoses, mucopolysaccharidoses, multi-infarct dementia, multifocal motor neuropathy, multiple sclerosis (MS), multiple systems atrophy (MSA-C and MSA-P), multiple system atrophy with orthostatic hypotension, muscular dystrophy, myasthenia-congenital, myasthenia gravis, myelinoclastic diffuse sclerosis, myoclonic encephalopathy of infants, myoclonus, myopathy-congenital, myopathy-thyrotoxic, myopathy, myotonia congenita, myotonia, narcolepsy, neuroacanthocytosis, neurodegeneration with brain iron accumulation, neurofibromatosis, neuroleptic malignant syndrome, neurological complications of AIDS, neurological manifestations of Pompe Disease, neuromyelitis optica, neuromyotonia, neuronal ceroid lipofuscinosis, neuronal migration disorders, neuropathy-hereditary, neurosarcoidosis, neurotoxicity, nevus cavernosus, Niemann-Pick Disease, O'Sullivan-McLeod Syndrome, occipital neuralgia, occult spinal dysraphism sequence, Ohtahara Syndrome, olivopontocerebellar atrophy, opsoclonus myoclonus, orthostatic hypotension, Overuse Syndrome, pain-chronic, paraneoplastic syndromes, paresthesia, Parkinson's Disease, parmyotonia congenita, paroxysmal choreoathetosis, paroxysmal hemicrania, Parry-Romberg, Pelizaeus-Merzbacher Disease, Pena Shokeir II Syndrome, perineural cysts, periodic paralyses, peripheral neuropathy, periventricular leukomalacia, persistent vegetative state, pervasive developmental disorders, phytanic acid storage disease, Pick's Disease, Piriformis Syndrome, pituitary tumors, polymyositis, Pompe Disease, porencephaly, Post-Polio Syndrome, postherpetic neuralgia, postinfectious encephalomyelitis, postural hypotension, postural orthostatic tachycardia syndrome, postural tachycardia syndrome, primary lateral sclerosis, prion diseases, progressive hemifacial atrophy, progressive locomotor ataxia, progressive multifocal leukoencephalopathy, progressive sclerosing poliodystrophy, progressive supranuclear palsy, pseudotumor cerebri, pyridoxine dependent and pyridoxine responsive seizure disorders, Ramsay Hunt Syndrome Type I, Ramsay Hunt Syndrome Type II, Rasmussen's Encephalitis and other autoimmune epilepsies, reflex sympathetic dystrophy syndrome, refsum disease-infantile, refsum disease, repetitive motion disorders, repetitive stress injuries, restless legs syndrome, retrovirus-associated myelopathy, Rett Syndrome, Reye's Syndrome, Riley-Day Syndrome, SUNCT headache, sacral nerve root cysts, Saint Vitus Dance, Salivary Gland Disease, Sandhoff Disease, Schilder's Disease, schizencephaly, seizure disorders, septo-optic dysplasia, severe myoclonic epilepsy of infancy (SMEI), shaken baby syndrome, shingles, Shy-Drager Syndrome, Sjogren's Syndrome, sleep apnea, sleeping sickness, Soto's Syndrome, spasticity, spina *bifida*, spinal cord infarction, spinal cord injury, spinal cord tumors, spinal muscular atrophy, spinocerebellar atrophy, Steele-Richardson-Olszewski Syndrome, Stiff-Person Syndrome, striatonigral degeneration, stroke, Sturge-Weber Syndrome, subacute sclerosing panencephalitis, subcortical arteriosclerotic encephalopathy, Swallowing Disorders, Sydenham Chorea, syncope, syphilitic spinal sclerosis, syringohydromyelia, syringomyelia, systemic lupus erythematosus, Tabes Dorsalis, Tardive Dyskinesia, Tarlov Cysts, Tay-Sachs Disease, temporal arteritis, tethered spinal cord syndrome, Thomsen Disease, thoracic outlet syndrome, thyrotoxic myopathy, Tic Douloureux, Todd's Paralysis, Tourette Syndrome, transient ischemic attack, transmissible spongiform encephalopathies, transverse myelitis, traumatic brain injury, tremor, trigeminal neuralgia, tropical spastic paraparesis, tuberous sclerosis, vascular erectile tumor, vasculitis including temporal arteritis, Von Economo's Disease, Von Hippel-Lindau disease (VHL), Von Recklinghausen's Disease, Wallenberg's Syndrome, Werdnig-Hoffinan Disease, Wemicke-Korsakoff Syndrome, West Syndrome, Whipple's Disease, Williams Syndrome, Wilson's Disease, X-Linked Spinal and Bulbar Muscular Atrophy, and Zellweger Syndrome.

The disclosed dosage forms and methods are expected to be especially useful for treating neurodegenerative diseases and neuroinflammatory disorders selected from the group comprising or consisting of: Alzheimer's disease, Parkinson's disease, Creutzfeldt Jakob disease (CJD), new variant of Creutzfeldt Jakobs disease (nvCJD), Hallervorden Spatz disease, Huntington's disease, multisystem atrophy, dementia, frontotemporal dementia, motor neuron disorders of multiple spontaneous or genetic background, amyotrophic lateral sclerosis (ALS), spinal muscular atrophy, spinocerebellar atrophies (SCAs), schizophrenia, affective disorders, major depression, meningoencephalitis, bacterial meningoencephalitis, viral meningoencephalitis, CNS autoimmune disorders, multiple sclerosis (MS), acute ischemic/hypoxic lesions, stroke, CNS and spinal cord trauma, head and spinal trauma, brain traumatic injuries, arteriosclerosis, atherosclerosis, microangiopathic dementia, Binswanger' disease (Leukoaraiosis), cochlear degeneration, cochlear deafness, AIDS-related dementia, fragile X-associated tremor/ataxia syndrome (FXTAS), progressive supranuclear palsy (PSP), striatonigral degeneration (SND), olivopontocerebellear degeneration (OPCD), Shy Drager syndrome (SDS), age dependant memory deficits, neurodevelopmental disorders associated with dementia, Down's Syndrome, synucleinopathies, superoxide dismutase mutations, trinucleotide repeat disorders as Huntington's Disease, trauma, hypoxia, vascular diseases, vascular inflammations, CNS-ageing. Also age dependent decrease of stem cell renewal may be addressed.

The disclosed dosage forms and methods are expected to be especially useful for treating neurodegenerative diseases and neuroinflammatory disorders selected from the group comprising or consisting of: Alzheimer's disease, Parkinson's disease, Huntington's disease, amyotrophic lateral sclerosis (ALS), hydrocephalus, CNS and spinal cord trauma such as spinal cord injury, head and spinal trauma, brain traumatic injuries, cochlear deafness, AIDS-related dementia, trinucleotide repeat disorders as Huntington's Disease, and CNS-aging.

The words "treatment", "treating" and variations thereof refer to curing, mitigating or relieving symptoms of a disease, medical condition or injury.

As used herein, a film layer that is "unbuffered" is a film layer that does not contain a weak acid or weak base that is effective to maintain pH near a chosen value upon addition of another acid or base. Stated differently, the unbuffered film layer does not contain a buffering agent, such as borates, citrates, or phosphates.

Enteral delivery refers to passing the active agent through the gastrointestinal tract, either naturally via the mouth and esophagus, or through an artificial opening (e.g., stoma) and absorbing the active agent in the intestine.

Leukotriene inhibitions include leukotriene receptor antagonists and/or leukotriene synthesis inhibitors that block 5-lipoxygenase activity. Such leukotriene inhibitors include, but are not necessarily limited to, leukotriene receptor antagonist such as Montelukast, Zafirlukast, Pranlukast, cinalukast, probilukast, iralukast and sulukast. Active agents capable of existing in various forms, such as base form, salts, esters, prodrugs, etc., are, unless otherwise indicated, encompassed by reference to the base drug. For example, the term "Montelukast" is intended to encompass all forms, including salts (e.g., Montelukast sodium), esters and prodrugs.

The term "amorphous" refers to a non-crystalline form of the solid i.e. a state that lacks the regular crystalline organization of atoms. Amorphous solids are generally more soluble, faster dissolving, easier to absorb in the GI tract or oral cavity and less stable than their crystalline counterparts. The amorphous content (amorphicity) of a solid can be accurately and precisely assessed using a number of well-established methodologies, including isothermal calorimetry, Powder X-ray diffraction (PXRD), Raman Spectroscopy, Differential Scanning Calorimetry (DSC), Continuous Relative Humidity Perfusion Microcalorimetry (cRHp), and Dynamic Vapor Sorption (DVS). In this document, the term amorphous also refers to an active agent(s) that exhibits 30% or more than 30% of amorphous material, more preferably above 50%.

The term "active agent(s)" or API (active pharmaceutical ingredient) refers mainly to pharmaceutically active ingredients, but may also refer to generally any agent(s) that chemically interacts with the subject to which it is administered to cause a biological change, such as, but not limited to eliminating symptoms of disease or regulating biological functions.

The term "stable" refers to a product which exhibit no or very limited changes in the dissolution profile and recovery (or assay) when the product is exposed to normal stability conditions (example 25° C./60% RH and 40° C./75% RH) for extended period of time.

An "oral film dosage form" generally refers to an edible composition that can be ingested by a subject (human or animal) to orally, buccally or sublingually administer a predetermined amount of an active agent(s) to the subject, wherein the composition is in the form of a film.

The "surface pH" is the pH measured on a surface of the film, such as the top or bottom surface of a monolayer film or on an exposed surface of the layer containing the active in a multilayer oral film. The film is prepared for pH testing by slightly wetting the film (adding water as needed for a pH test—e.g. one to three drops). The pH is then measured by bringing the electrode in contact with the surface of the oral film. This measurement of the surface pH is preferably performed on several films of the same formulation.

The terms "film" and "film layer" refer to a component or layer of dosage form that is distinctly different from pills, tablets, caplets, and capsules, and in which the dosage form is a thin strip of material. Such films are typically rapidly disintegrating or rapidly dissolving, but can also exhibit longer disintegration and/or dissolution time when required. The films are generally sufficiently flexible to allow bending or even folding without breaking. A film layer is a sheet-like material having a thickness that is much less than its length or width. For example, oral transmucosal devices typically have a thickness on the order of about 50 μm to 500 μm (i.e., 0.05 mm to 0.5 mm), although thicker or thin films may be suitable; and width and length dimensions typically on the order of about 5 mm to 40 mm, although larger or smaller dimensions can be used.

Throughout this disclosure, unless otherwise indicated, it will be appreciated that specific reference to "MTL" or "Montelukast" implies that other leukotriene receptor antagonists may be substituted.

The film dosage form can comprise a single film layer, or multiple layers. For example, in the case of buccal or sublingual film dosage forms, it can be beneficial to employ a biocompatible layer (e.g., a bioadhesive layer) containing the active agent and a non-adhesive barrier layer to prevent or reduce ingestion of the active agent(s) and ensure that all or most of the active agent crosses the mucous membrane to which the bioadhesive layer is applied. The term "bioadhesive" means that the composition of the film layer is formulated to adhere to the selected mucous membrane through which delivery of the active agent is targeted, and encompasses the term "mucoadhesive." For example, bioadhesive polymers used in formulating the film should be selected to exhibit adequate adhesion within the environment at the targeted mucous membrane to ensure that the bioadhesive layer remains in contact with the mucous membrane to which it is applied and allows the active agent to directly enter the blood stream through the mucous membrane.

The active agent can be combined or blended with film forming polymers and/or bioadhesive polymers to obtain a balanced combination of properties like flexibility, tensile strength, uniformity of the film and the drug, hydration speed, drug release, disintegration time, palatability (taste, smell, texture and aftertaste), mouth feel, mucoadhesion, and chemical and physical stability suitable for an oral delivery device.

Examples of suitable film forming polymers exhibiting bioadhesion include hydroxypropyl cellulose, hydroxymethylcellulose, natural or synthetic gum, polyvinyl alcohol, polyethylene oxide, homo- and copolymers of acrylic acid crosslinked with a polyalkenyl polyether or divinyl alcohol, polyvinylpyrrolidone, hydroxypropylmethyl cellulose, sodium alginate, pectin, gelatin maltodextrins chitosan, and poly-lysines. In certain embodiments or aspects of this disclosure, the active agent can be combined with film forming neutral polysaccharides such as pullulan.

Penetration enhancing agents can also or alternatively be employed to further increase the rate and/or total amount of absorption of the active agent. Examples of penetration enhancers that can be advantageously employed include 2,3-lauryl ether, phosphatidylcholine, aprotinin, polyoxyethylene, azone, polysorbate 80, benzalkonium chloride, polyoxyethylene, cetylpyridinium chloride, phosphatidylcholine, cetyltrimethyl ammonium bromide, sodium EDTA, cyclodextrin, chitosan, sodium glycocholate, dextran sulfate 16 sodium glycodeoxycholate. Other penetration enhancers include surfactants, bile salts (by extracting membrane protein or lipids, by membrane fluidization, by producing reverse micellization in the membrane and creating aqueous channels), fatty acids (that act by disrupting intercellular lipid packing), azone (by creating a region of fluidity in intercellular lipids), pore forming agents (e.g., molecules, peptides, nucleic acids or particles that insert into the lipid membrane and create a hole through which the API can pass) and alcohols (by reorganizing the lipid domains and by changing protein conformation), sulphoxides (dimethylsulphoxide, decylmethyl sulfoxide), pyrrolidones (2pyrrolidone, 2P), alcohols/alkanols (ethanol or decanol), glycols (propylene glycol), terpenes (1,8-cineole, menthol, and menthone, D-limonene), fatty acids (oleic acid, sodium caprate), and bile salts (sodium deoxycholate, sodium deoxyglycocholate). It was found that the permeation and absorption is greatly enhanced through the use of a single or combination of penetration enhancers present in the formulation in the range of 0.05-8.00% dry w/w.

Examples of Anti-oxidants and chelating agents that can be advantageously employed comprise disodium-EDTA, sodium calcium EDTA, citric acid, L-cystein, vitamin E, ascorbyl palmitate, butylated hydroxyanisole, butylated hydroxytoluene, potassium metabisulfite, propyl gallate, sodium metabisulfite, sodium thiosulfate, 3,4-dihydroxybenzoic acid.

Examples of surfactants that can be employed to enhance penetration and/or wettability of the film to promote adhesion, include polysorbates (Tween™, Span™), sodium dodecyl sulfate (sodium lauryl sulfate), lauryl dimethyl amine oxide, cetyltrimethylammonium bromide (CTAB), polyethoxylated alcohols, polyoxyethylene sorbitan octoxynol (Triton X100™), N,N-dimethyldodecylamine-N-oxide, hexadecyltrimethylammonium bromide (HTAB), polyoxyl 10 lauryl ether, Brij 721™, bile salts (sodium deoxycholate, sodium cholate) polyoxyl castor oil (Cremophor™), nonylphenol ethoxylate (Tergitol™), cyclodextrins, lecithin, methylbenzethonium chloride (Hyamine™).

The solubility and disintegration profiles of the film can influence the bioavailability of the drug. Therefore, certain embodiments of the film platform will contain specific quantities of disintegrants to control the residence time of the film in the oral cavity. Certain forms of the drug product may contain between 0-10% by mass of a disintegrant. Examples of disintegrants that could be used are Maltodextrin, Citric acid, Sodium starch, glycolate, crosslinked polyvinylpyrrolidone (crospovidone), crosslinked sodium carboxymethyl cellulose, Calcium silicate, Alginic acid, and vinylpyrrolidone-vinyl acetate copolymers.

The term "pre-solubilized" as used herein refers to a dosage form comprising an active agent that undergoes a phase transformation in the oral cavity upon administration. For instance, a pre-solubilized form of MTL could be a precipitated MTL previously administered as a solubilized MTL in a film matrix. The pre-solubilized precipitate is not dissolved, but is in a form (e.g., very small particles dispersed in a liquid) that is susceptible to rapid dissolution, such as upon exposure to the higher pH environment of the intestine.

The term "matrix" or "film matrix" refers to the surroundings or medium constituting the film layer in which the active agent (e.g., Montelukast) is solubilized or distributed, and generally comprises a mixture of polymers and excipients. The film forming matrix supporting the API within the oral film dosage form can comprise about 40.0-99.0% dry w/w of the film layer.

Stability enhancing agents can be added to the film to prevent photodegradation, oxidation, and/or microbial contamination. Photodegradation inhibitors include ultraviolet radiation absorbers and pigments. Ultraviolet absorbers include hydroxyl benzophenones and hydroxyphenyl benzotriazoles. Pigments that can be added to the film include various metal oxides, such as titanium dioxide ($TiO_2$), ferric oxide ($Fe_2O_3$), iron oxide ($Fe_3O_4$), and zinc oxide (ZnO). In the cases of oral film dosage form the potential of photodegradation of the film dosage form may be mitigated by the use of individual pouches as the final packaging material. According to one embodiment, the pouches are made out of laminated material, comprising some aluminum or reflective foil material preventing photodegradation of the film and products contained therein. Microbial contamination may be controlled by the use of antimicrobial agent such as methyl, ethyl or propyl paraben, sodium benzoate, benzoic acid, sorbic acid, potassium sorbate, propionic acid or a combination of the above.

Other additives, such as excipients or adjuvants that can be incorporated into the film include flavors, sweeteners, coloring agents (e.g., dyes), plasticizers, and other conventional additives that do not deleteriously affect transmucosal delivery of the active agent, oral mucoadhesivity, or their important film properties.

The film can be used in a monolayer, bilayer or other multilayer form.

According to an embodiment, the bilayer film dosage form comprises a first layer having the API and a second layer having agents such as a taste-masking agent, backing agent for protecting the first layer, and/or a permeation enhancer. The second layer can also be used to favor the directed absorption through the oral mucosa (unidirectional absorption). Other embodiments could have the same API or a different API present in the second layer to enterally deliver the active with a controlled release profile. Alternatively, an active agent in the second layer could be used to modify the absorption of the active agent in the first layer.

A safe and effective amount generally refers to an amount that provides a beneficial or therapeutic effect, i.e., provides a curing or mitigating effect on disease or disease symptoms, but which is sufficiently low to avoid severe or life-threatening side effects when the active agent is administered and delivered transmucosally and/or enterally.

Figure 6:
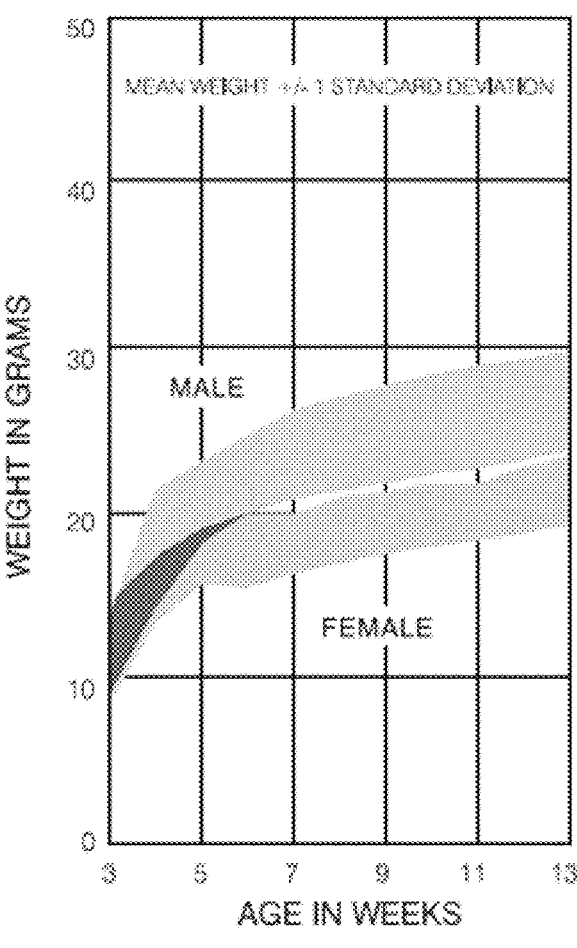
FIG. 6 is a graph of body weight verses age of C57/B16 mice from Charles River.

Montelukast solubility in aqueous media is dependent on the pH. It has been found that MTL exhibits increasing solubility at alkaline (basic) pH above 7.5 and is found to rapidly precipitate in media below pH 7.5. This has been experimentally shown by Okumu et al (Okumu, Pharm. Res, 25, 12, 2008), see FIG. 6, where MTL alone or in the presence of surfactants only displays a marked increase in solubility above pH 7.5. This study has also shown that although the impact of surfactants may marginally increase MTL solubility, it is only at alkaline (basic) pH environments that MTL readily solubilizes. Nevertheless, other parameters than solubility can influence the dissolution rate of the Montelukast i.e., the dosage form appears to have a significant impact on the dissolution rate. In certain embodiments the Montelukast is present as a dissolved form in the dosage form matrix which will dissolve and/or disintegrate in the mouth to allow the MTL to precipitate in saliva before being swallowed. Conversely, FIG. 1, is showing the schematic representation of the dissolution of an oral dosage form of MTL, such as a conventional tablet. FIG. 1A depicts the initial disintegration of the tablet in the stomach. FIG. 1B depicts the tablet disintegration after 10-15 minutes, where due to slower disintegration, the tablet pieces remain concentrated in a localized cluster limiting the dissolution and potential absorption. This limiting impediment is further exacerbated due to the poor solubility of MTL in acidic environments such as the stomach. Since MTL has an especially low solubility at low pH, the high concentration of MTL following disintegration of the tablet further increases the insolubility of MTL thereby potentially further reducing the bioavailability of the API.

In certain embodiments, the active agent can be distributed in the film matrix in the form of micro- or nano-particles.

Figure 2:
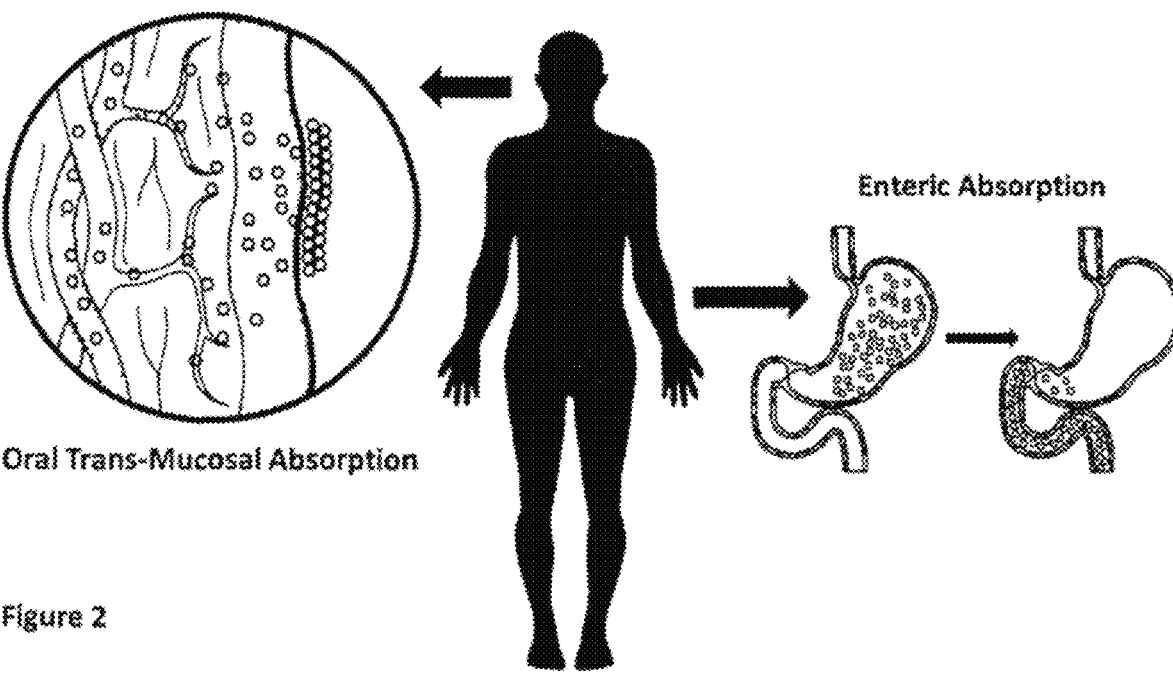
FIG. 2 is an illustrative representation of the absorption or an oral film dosage form when administered to a subject.
Figure 3:
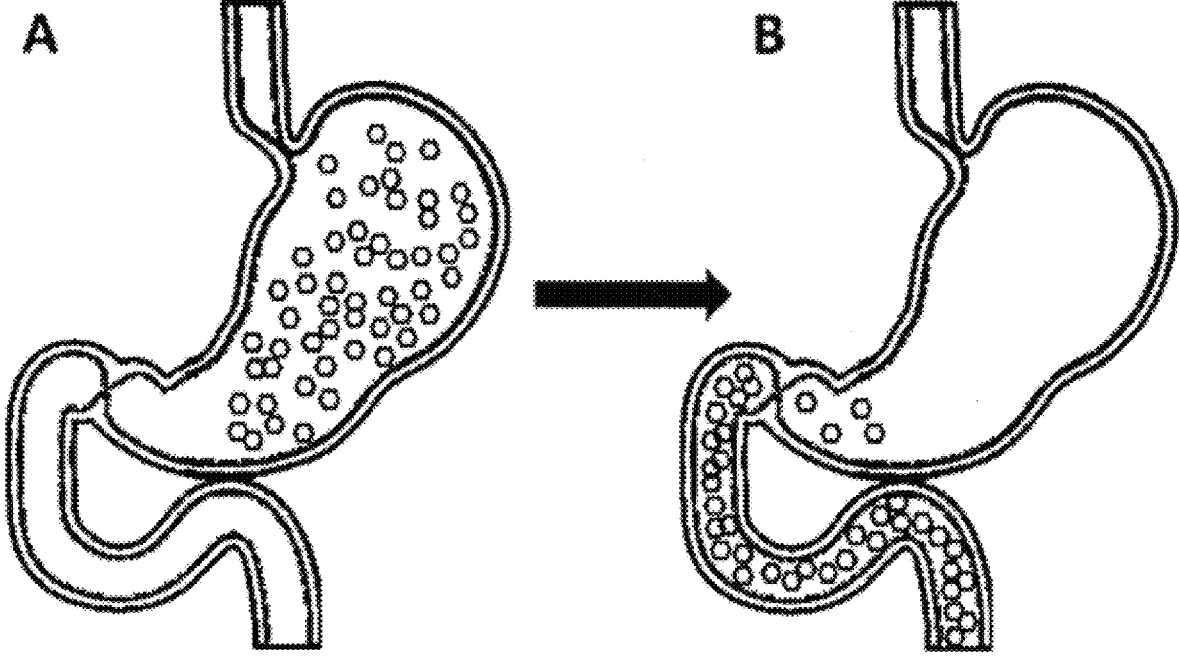
FIG. 3 is an illustrative representation of the behavior of the active in the stomach following administration of the oral film to a subject.
Figure 4:
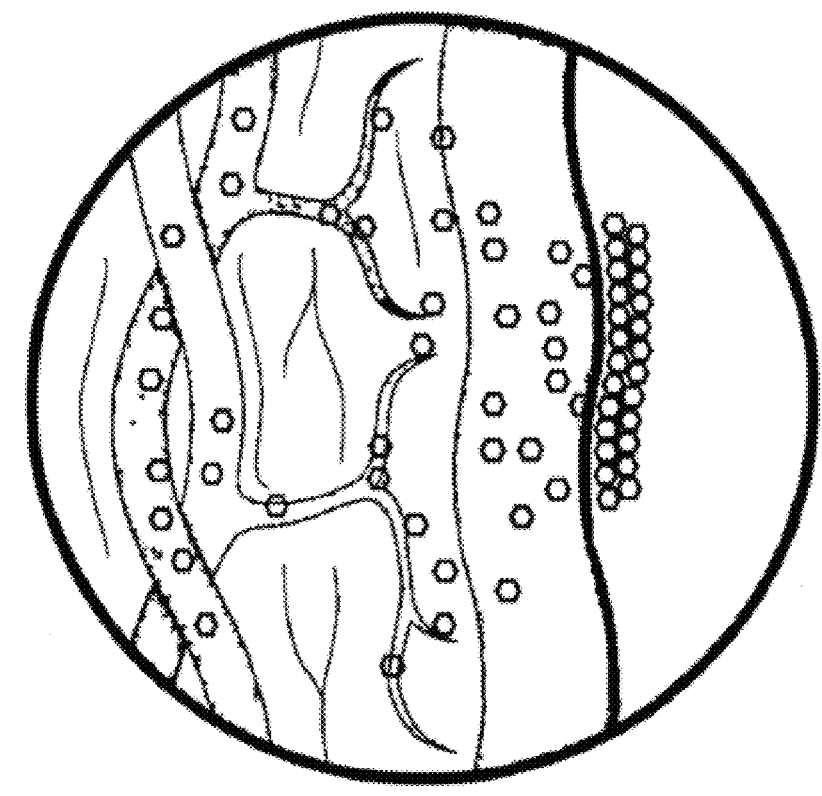
FIG. 4 is an illustrative representation of the transmucosal absorption following administration of the oral film to a subject.

According to an aspect of the present disclosure, to mitigate the shortcomings of the abovementioned Montelukast tablet oral dosage form, it is herein disclosed a film oral dosage form wherein a leukotriene receptor antagonist (e.g., MTL) is administered via enteric absorption (FIG. 2B) alone or in combination with oral transmucosal and/or sublingual absorption (FIG. 2A) In certain embodiments, the film oral dosage form is designed to disintegrate in the mouth and allow a solubilized active agent to precipitate in the mouth and be swallowed, thereby delivering the API into the stomach as a fine precipitate suspended in aqueous medium. Referring now to FIG. 3A, upon reaching the stomach, the swallowed API precipitate in suspension is significantly more homogenously distributed throughout the stomach compared to the slowly disintegrating tablet dosage form which enters the stomach in relatively large solid particles or fragments containing the active agent. In this way, uptake of the film oral dosage form is believed to be less limited by the gastric emptying cycles. The lack of solid matrix retaining the API favors transport of the API throughout the stomach thus mitigating the effect of the low solubility of the API at low pH. As per the dissolution profile (FIG. 1(5)) which clearly shows that once the dosage form is dissolved and/or disintegrated and the MTL precipitates in the saliva, its rate of dissolution in the intestine is much faster compared to that of the tablet. It is hypothesized that the precipitated MTL in saliva has a much smaller particle size and can escape the stomach via the pylorus as very fine particles suspended in a liquid, allowing for faster and higher absorption.

In certain embodiments, the film layer containing the active agent dissolves and/or disintegrates in the oral cavity upon contact with saliva. While the film dissolves and/or disintegrates, the Montelukast (or other leukotriene receptor antagonist) precipitates in the saliva (Montelukast API precipitates below pH 8) thus forming an API precipitate suspension in the saliva. The suspended API is then swallowed and reaches the stomach as a dispersed precipitate, improving the bioavailability of the Montelukast API. The pre-solubilized film at least mitigates the dissolution problem associated with the poor solubility of Montelukast in the patient's acidic stomach conditions. The poor solubility is generally amplified by the presence of a concentrated form of MTL. Though buccal and/or sublingual absorption may arise, the drug is predominantly absorbed enterally. As such, the oral film dosage can be used to overcome the solubility problem encountered when having Montelukast sodium present in the stomach in a solid or undissolved form. According to an embodiment of the disclosed oral dosage form, Montelukast film particulates reach the stomach already in a suspended/precipitated form, meaning that the Montelukast that is solubilized in the dosage form precipitates in the oral cavity and/or esophagus, resulting in a suspended Montelukast precipitate being delivered to the stomach. As such, the pre-solubilized Montelukast in the dosage form has an improved bioavailability derived at least in part from the fact that the API is delivered to the stomach in a dispersed and thus less concentrated form than conventional tablets. The suspended precipitate thus exhibits an improvement in bioavailability when compared with tablets which must initially be dissolved in the stomach before being absorbed. The improved bioavailability can lead to increased transport of the active agent across the blood-brain barrier, allowing lower doses and/or more effective treatment. The administration of a Montelukast API suspension to the stomach at least mitigates solubility related problems arising in or with other Montelukast oral dosage forms such as swallowable and chewable tablets. Yet, according to an embodiment of the present invention, the administration of the suspended form through a film dosage form at least mitigates stability problems typically associated with API administered through liquid medium. In addition, the orally precipitated Montelukast is likely able to reach the small intestine quicker through the pylorus than other oral dosage forms of Montelukast or other Leukotriene receptor antagonist. According to an aspect of the present disclosure, using the preferred oral film dosage form, a dosage of up to a maximum of 70 mg a day of Montelukast is sufficient to alleviate symptoms or treat conditions associated with neuroinflammation. An essential element of such oral film dosage form is its ability to maintain Montelukast in a condition promoting its solubility, i.e. alkaline pH. According to some embodiments, the Montelukast oral film has an alkaline surface. The alkaline surface pH signifies that the film maintains Montelukast under alkaline conditions favoring its solubility and preventing recrystallization of the Montelukast. Recrystallization of the Montelukast is associated with unstable oral films. The Montelukast oral film preferably has a surface pH greater than to pH 7.5, preferably greater than 8.5 and more preferably greater than 9.

Another embodiment of the oral dosage form comprises a capsule dosage form (e.g., a gelatin or cellulose-base capsule) containing the leukotriene inhibitor solubilized or distributed as an amorphous precipitate in a polymer matrix that disintegrates or dissolves in an aqueous medium. According to this dosage form, the oral dosage form of Montelukast is taken orally by the patient. Upon reaching the stomach the capsule shell is solubilized thus delivering the solubilized or amorphous precipitate of Montelukast (or other leukotriene receptor antagonist) into the aqueous medium of the stomach. Such precipitate will be rapidly distributed throughout the stomach and mitigates the shortcoming related to tablets and chewables. Since the active agent is already in a liquid medium in a solubilized or amorphous precipitate in suspension form, the oral capsule dosage form effectively mitigates low dosage bioavailability problems. Therefore, the Montelukast capsule allow the Montelukast to reach the stomach as a pre-solubilized, amorphous precipitate in suspension. It is possible that the stomach conditions, unfavorable to the dissolution of Montelukast tablets and chewables, result in some precipitation of the Montelukast in the stomach. However, since the Montelukast is already in a solubilized form or dispersed precipitate in aqueous medium, the extent of precipitation should be less than the loss of efficacy associated with the need to solubilize the Montelukast tablet in the stomach.

Leukotriene blockers or inhibitors (i.e., leukotriene receptor antagonists and leukotriene synthesis inhibitors) can function to improve cognitive impairment by reducing the neuroinflammatory response within the brain. Leukotriene blockers, such as MTL, must therefore cross the blood-brain barrier and accumulate in the CSF. Consequently, during clinical trials, patients were tested for CSF levels of MTL after 3 and 7 hours respectively, (see Table 1). What is most surprising about this finding is that between the 3- and 7-hour test points, the concentration of MTL continued to increase. This is particularly unexpected as the plasma levels show a Tmax value between 2-4 hours indicating that the maximum accumulated concentration is rapidly reached in the blood. The rapid accumulation of the Montelukast in the patients' blood is attributable to the enteral administration of Montelukast delivered to the stomach as an amorphous precipitate suspended in aqueous medium. As only two data points were taken during our clinical study it remains unclear if the time point at 7 hours represents the Cmax, or if the Cmax occurs after 7 hours as more MTL accumulates but is cleared at a much slower rate. This is of great significance when compared to the known treatments, wherein a strict regimen of continuous dosing was required to maintain effective levels of MTL for cognitive improvement.

An effective concentration of Montelukast in the CSF is obtained via administration of the Montelukast according to the disclosed methods and dosage forms. Sufficient level of Montelukast is attained in the CSF because the Montelukast reaches the stomach in a pre-solubilized form thereby enhancing the absorption and bioavailability of the Montelukast. Accordingly, a disclosed method of treating neurodegenerative or neuroinflammatory disorder comprises the step of enterally delivering to a person or other animal in need of treatment for a neurodegenerative disease or neuroinflammatory disorder via a film dosage form, a safe and effective amount of solubilized Montelukast.

Our data clearly demonstrates that regular dosing of Montelukast oral film every 2 hours is not necessary to maintain effective levels of MTL in the CSF. The higher bioavailability of the Montelukast in the CSF is due to the administration of Montelukast in such a dosage that the active agent is delivered to the stomach as a suspended precipitate in aqueous medium, thus mitigating the hurdles related to solubilizing Montelukast swallowable tablets or chewable tablets in the stomach. Accordingly, administering Montelukast under a liquid dosage form or a dosage form for buccal dissolution wherein the API precipitates in the saliva and yields an API suspension in saliva, increases the bioavailability of Montelukast in the subjects. It is thus desired to administer a form of Montelukast (or other leukotriene receptor antagonist) orally for dissolution or disintegration of the oral dosage form before reaching the stomach.

TABLE 1

| Pharmacokinetic Data for CSF Concentrations | | |
| --- | --- | --- |
| Sample | Concentration at 3 hours (ng/ml) | Concentration at 7 hours (ng/ml) |
| MTL03 Film | 3.60 | 4.20 |

We have performed a clinical study of our product to determine the pharmacokinetics of the API loaded into this pharmaceutical platform. Our film product and the Singulair® product both contain 10 mg MTL free base. Singulair® is the marketed formulation of MTL, commonly prescribed for asthma sufferers. It consists of a 10 mg loaded API tablet. The Cmax and Tmax values are listed below, see Table 2. Results indicate that we have approximately 1.5 times the Cmax and AUC values compared to the Singulair® reference. These higher values for our films means that we could load less API into the film product and achieve the same Cmax/AUC as the Singulair® reference product. The major difference between the disclosed Intelgenx prototype and Singulair® is the physical state of the MTL once it reaches the stomach. In the Singulair® product, the MTL reaches the stomach in a compressed solid state and thus must solubilize in the stomach under unfavorable conditions. In contrast, the disclosed MTL03 oral film dosage form comprises solubilized MTL, which is placed in the mouth and allowed to dissolve before being swallowed. Upon dissolution of the disclosed MTL03 oral film dosage form, the MTL precipitated in the oral cavity while the remainder of the dosage form disintegrated and/or dissolved, creating a MTL precipitate ultimately suspended in aqueous medium (i.e. saliva). As such, the MTL contained within the disclosed MTL03 prototype reaches the stomach in an already pre-solubilized state, meaning that the matrix has been dissolved or disintegrated, exposing the MTL precipitate to the stomach fluid. The MTL is then transferred to the small intestine via the pylori. Since the MTL is already present as a suspended precipitate, the MTL may more easily reach the small intestine through the leaking pylori. It is well known that the pylori is not leak proof and allows some liquid to flow through even in its closed position. As such, MTL of the disclosed MTL03 film dosage once in the stomach is believed to more easily traverse the pylori. Administering MTL enterally as a suspended precipitate in aqueous medium improves bioavailability. To further support the fact that MTL exhibits increased bioavailability when administered through such dosage form, we compared the pharmacokinetics of MTL provided to the FDA under New Drug Application (NDA) 020830 (see Table 2). Table 2 shows that the chewable oral dosage form is more readily bioavailable than the solid dosage. The chewable MTL dosage is partly solubilized, hence its bioavailability is superior to the tablet bioavailability. In particular, the chewable dosage form is about 1.17 times more bioavailable than the tablet when administered in a fasting subject (compared using available bioavailability date shown in Table 2). Therefore, through comparative extrapolation, the disclosed MTL03 film dosage which contains MTL solubilized in the film matrix and precipitates in the saliva once the matrix dissolves has proven to be 1.5 times more bioavailable than the tablet when comparing the area under the curve (AUC) (see Tables 3 & 4). It is believed that administering the MTL as a precipitate suspension that is free from the film or tablet matrix improves the bioavailability of the MTL when compared with the corresponding tablet and chewable. This improved bioavailability is believed to be at least in part caused by the increased contact area of the precipitate API. In addition, the MTL is delivered in the stomach in a less concentrated manner than corresponding tablet and chewable oral dosage forms (see FIGS. 1 and 3).

TABLE 2

| Bioavailability comparison between the tablet and the chewable oral dosage forms | |
| --- | --- |
| Dosage form | Bioavailability |
| Singulair ® Film coated tablet | 64% (not affected by food) |
| Chewable | 75% (fasted) 63% (with food) |

According to an embodiment, the method for treating a neurodegenerative disease or neuroinflammatory disorder, comprises the step of (a) enterally delivering to a person or other animal in need of treatment for a neurodegenerative disease or neuroinflammatory disorder via a film dosage form, a safe and effective amount of Montelukast. Preferably, the Montelukast is orally administered via an oral film dosage comprising MTL or any other suitable salt, ester or prodrug thereof. According to the present method of treatment, the Montelukast is at least substantially solubilized in the film dosage form and administered orally with a film matrix that dissolves and/or disintegrates in contact with aqueous medium such as saliva when in the oral cavity. The MTL precipitates upon dissolution of the film matrix in the saliva in the person's or animal's oral cavity. Furthermore, the pharmacokinetic data for the disclosed MTL03 MTL dosage form show that absorption is significantly higher than for the branded form Montelukast Singulair® product (tablet). Therefore administering MTL as a film dosage form having a matrix that rapidly dissolves or disintegrates (i.e. that dissolved or disintegrates within less than 10 minutes, preferably between 2 and 7 minutes and more preferably within 3 to 5 minutes) to yield a precipitate suspension in aqueous medium before reaching the stomach, markedly improves the bioavailability of Montelukast, as compared to oral tablets or capsules where Montelukast is held in a dosage form matrix that is resistant to solubilization and absorption of the active agent. According to a preferred aspect of the present disclosure, a leukotriene receptor antagonist, such as Montelukast, is solubilized in the oral film dosage form.

According to another aspect of the present disclosure, the leukotriene receptor antagonist is present in the film as a particulate active in an oral film dosage form. In such an alternate embodiment of the disclosure, this particulate API is held in the oral film matrix, in which the film matrix will dissolve and/or disintegrate when in contact with an aqueous medium (i.e. saliva). Upon dissolution and/or disintegration of the film matrix, the particulate API will be present as a particulate suspension in aqueous medium. The particulate API is preferably in amorphous form in the film matrix.

TABLE 3

| Pharmacokinetic Data for Plasma Concentrations | | | |
|---|---|---|---|
| Sample | Cmax (ng/ml) | Tmax (hrs) | AUC |
| MTL03 Film (alkaline) | 599 | 2.70 | 3910 |
| Singulair ® product | 386 | 3.63 | 2617 |
| Ratio alkaline Film/Tablet | 1.55 | 0.74 | 1.49 |

TABLE 4

| Comparison of bioavailability between different dosage forms | |
|---|---|
| Dosage form | Bioavailability |
| Singulair ® tablet product | 1 |
| MTL03 Film | 1.5 |

Once administered, the oral film is preferably applied against the subjects' oral mucosa where it will be adhered to and enter in contact with the subject's saliva. Contact between the film and the saliva dissolves and/or disintegrates the film in the oral cavity. The dissolved and/or disintegrated oral film matrix advantageously allows precipitation of the active agent in the oral cavity of a subject. The precipitate is swallowed for enteral administration as a suspended precipitate in aqueous medium.

According to embodiments, a preferred amount of MTL per unit dosage form is from about 10 mg to about 75 mg, preferably about 20 mg to about 60 mg, more preferably about 30 mg to about 50 mg.

Illustrative, but non-limiting, examples of formulations used to prepare a MTL oral films is shown in Tables 5-11.

TABLE 5

| | | MTL01 | | |
|---|---|---|---|---|
| Item # | Description | Function | Composition (% wet w/w) | Composition % dry (w/w) |
| A | Methanol | Solvent (will be removed during manu-facturing) | 0.29 | — |
| B | Purified Water | Solvent (will be removed during manu-facturing) | 79.68 | — |
| 1 | Starch | Filler | 1.81 | 9.04 |
| 2 | HPC SL | Film former polymer | 8.37 | 41.79 |
| 3 | Xanthan gum | Thickener | 0.88 | 4.39 |
| 4 | Sucralose | Sweetener | 0.44 | 2.20 |
| 5 | Glycerol | Plasticizer | 1.85 | 9.24 |
| 6 | Montelukast Sodium | Active | 3.3 | 16.48 |
| 7 | Ascorbic acid | Stabilizer | 0.01 | 0.05 |
| 8 | Methylparaben | Anti-microbial agent | 0.11 | 0.55 |
| 9 | Titanium Dioxide | Opacifier | 0.27 | 1.35 |
| 10 | Yellow #10 | Color | 0.28 | 1.40 |
| 11 | HPC LF | Film former polymer | 0.73 | 3.64 |
| 12 | Calcium Carbonate | pH Modifier | 0.51 | 2.55 |
| 13 | Sodium glycocholate | Permeation Enhancer | 1.47 | 7.34 |
| Total | | | 100 | 100.00 |

TABLE 6

| | | MTL02 | | |
|---|---|---|---|---|
| Item # | Description | Function | Composition (% wet w/w) | Composition % dry (w/w) |
| A | Methanol | Solvent (will be removed during manu-facturing) | 0.2 | — |
| B | Purified Water | Solvent (will be removed during manu-facturing) | 79.68 | — |
| 1 | Povidone | Film former polymer | 11.08 | 55.07 |
| 2 | Locust Bean Gum | Thickener | 0.88 | 4.37 |
| 3 | PEG 300 | Plasticizer | 0.15 | 0.75 |
| 4 | Labrafil M1944CS | Permeation Enhancer | 0.89 | 4.42 |
| 5 | Sucralose | Sweetener | 0.44 | 2.19 |
| 6 | Citric Acid | pH Modifier | 0.61 | 3.03 |
| 7 | Montelukast Sodium | Active | 3.3 | 16.40 |
| 8 | Sodium Edetate | Stabilizer | 0.01 | 0.05 |
| 9 | Propylparaben | Anti-microbial agent | 0.1 | 0.50 |

TABLE 6-continued

| | | MTL02 | | |
|---|---|---|---|---|
| Item # | Description | Function | Composition (% wet w/w) | Composition % dry (w/w) |
| 10 | Titanium Dioxide | Opacifier | 0.27 | 1.34 |
| 11 | Yellow #10 | Color | 0.28 | 1.39 |
| 12 | HPC-GXF | Film former polymer | 2.11 | 10.49 |
| Total | | | 100.00 | 100.00 |

TABLE 7

| | | MTL03 | | |
|---|---|---|---|---|
| Item # | Description | Function | Composition (% wet (w/w) | Composition % dry (w/w) |
| A | Methanol | Solvent (will be removed during manufacturing) | 0.29 | — |
| B | Purified Water | Solvent (will be removed during manufacturing) | 79.68 | — |
| 1 | Starch | Filler | 1.81 | 9.04 |
| 2 | Pullulan | Film former polymer | 8.37 | 41.79 |
| 3 | Tara gum | Viscosity Modifier | 0.88 | 4.39 |
| 4 | PEG 300 | Plasticizer | 0.15 | 0.75 |
| 5 | Sorbitol P60W | Plasticizer | 1.83 | 9.14 |
| 6 | Sucralose | Sweetener | 0.44 | 2.20 |
| 7 | Glycerol | Plasticizer | 1.85 | 9.24 |
| 8 | Montelukast Sodium | Active | 3.30 | 16.48 |
| 9 | BHT | Stabilizer | 0.01 | 0.05 |
| 10 | Propylparaben | Anti-microbial agent | 0.11 | 0.55 |
| 11 | Titanium Dioxide | Opacifier | 0.27 | 1.35 |
| 12 | Yellow #10 | Color | 0.28 | 1.40 |
| 13 | HPC LF | Film former polymer | 0.73 | 3.64 |
| Total | | | 100.00 | 100.00 |

TABLE 8

| | | MTL04 | | |
|---|---|---|---|---|
| Item # | Description | Function | Composition (% wet (w/w) | Composition % dry (w/w) |
| A | Methanol | Solvent (will be removed during manufacturing) | 0.29 | — |
| B | Purified Water | Solvent (will be removed during manufacturing) | 79.68 | — |
| 1 | Starch | Filler | 0.74 | 3.69 |
| 2 | PEO 200K | Film former polymer | 8.37 | 41.79 |
| 3 | PEO 100K | Film former polymer | 2.35 | 11.73 |
| 4 | Menthol | Flavor | 1.3 | 6.49 |
| 5 | Sorbitol P60W | Plasticizer | 1.68 | 8.39 |
| 6 | Sucralose | Sweetener | 0.44 | 2.20 |
| 7 | Citric Acid | pH Modifier | 0.45 | 2.25 |
| 8 | Montelukast Sodium | Active | 3.3 | 16.48 |

TABLE 8-continued

| | | MTL04 | | |
|---|---|---|---|---|
| Item # | Description | Function | Composition (% wet (w/w) | Composition % dry (w/w) |
| 9 | Sodium Sulfite | Stabilizer | 0.01 | 0.05 |
| 10 | Methylparaben | Anti-microbial agent | 0.11 | 0.55 |
| 11 | Titanium Dioxide | Opacifier | 0.27 | 1.35 |
| 12 | Yellow #10 | Color | 0.28 | 1.40 |
| 13 | HPC JF | Film former polymer | 0.73 | 3.64 |
| Total | | | 100.00 | 100.00 |

TABLE 9

| | | MTL05 | | |
|---|---|---|---|---|
| Item # | Description | Function | Composition (% wet (w/w) | Composition % dry (w/w) |
| A | Methanol | Solvent (will be removed during manufacturing) | 0.29 | — |
| B | Purified Water | Solvent (will be removed during manufacturing) | 78.66 | — |
| 1 | Sodium Hydroxide | pH Modifier | 0.65 | 3.09 |
| 2 | HPMC E5 | Film former polymer | 3.21 | 15.25 |
| 3 | HPC-L | Film former polymer | 9.63 | 45.75 |
| 4 | PEG 300 | Plasticizer | 0.15 | 0.71 |
| 5 | Sorbitol P60W | Plasticizer | 1.83 | 8.69 |
| 6 | Sucralose | Sweetener | 0.44 | 2.09 |
| 7 | Sodium Metabisulfite | Stabilizer | 0.59 | 2.80 |
| 8 | Montelukast Sodium | Active | 3.3 | 15.68 |
| 9 | Sodium Edetate | Stabilizer | 0.01 | 0.05 |
| 10 | Propylparaben | Anti-microbial agent | 0.11 | 0.52 |
| 11 | Yellow #10 | Color | 0.28 | 1.33 |
| 12 | Oleic acid | Permeation Enhancer | 0.85 | 4.04 |
| Total | | | 100.00 | 100.00 |

TABLE 10

| | | MTL06 | | |
|---|---|---|---|---|
| Item # | Description | Function | Composition (% wet (w/w) | Composition % dry (w/w) |
| A | Methanol | Solvent (will be removed during manufacturing) | 0.29 | — |
| B | Purified Water | Solvent (will be removed during manufacturing) | 79.68 | — |
| 1 | Sodium Hydroxide | pH Modifier | 0.84 | 4.19 |
| 2 | Pullulan | Film former polymer | 9.34 | 46.63 |
| 3 | Xanthan gum | Thickener | 1.88 | 9.39 |
| 4 | PEG 300 | Plasticizer | 0.15 | 0.75 |
| 5 | Sodium sulfite | Stabilizer | 0.65 | 3.25 |

TABLE 10-continued

| | | | MTL06 | |
|---|---|---|---|---|
| Item # | Description | Function | Composition (% wet (w/w) | Composition % dry (w/w) |
| 6 | Sucralose | Sweetener | 0.44 | 2.20 |
| 7 | Glycerol | Plasticizer | 1.85 | 9.24 |
| 8 | Montelukast Sodium | Active | 3.3 | 16.48 |
| 9 | Azone | Permeation Enhancer | 0.92 | 4.59 |
| 10 | Propylparaben | Anti-microbial agent | 0.11 | 0.55 |
| 11 | Titanium Dioxide | Opacifier | 0.27 | 1.35 |
| 12 | Yellow #10 | Color | 0.28 | 1.40 |
| Total | | | 100.00 | 100.00 |

TABLE 11

| | | | MTL07 | |
|---|---|---|---|---|
| Item # | Description | Function | Composition % wet (w/w) | Composition % dry (w/w) |
| A | Methanol | Solvent (will be removed during manufacturing) | 0.29 | — |
| B | Purified Water | Solvent (will be removed during manufacturing) | 79.68 | — |
| 1 | Ascorbic acid | Stabilizer | 0.97 | 4.84 |
| 2 | HPC-SL | Film former polymer | 9.66 | 48.23 |
| 3 | Xanthan gum | Thickener | 1.43 | 7.14 |
| 4 | PEG 300 | Plasticizer | 0.15 | 0.75 |
| 5 | Sorbitol P60W | Plasticizer | 1.83 | 9.14 |
| 6 | Sucralose | Sweetener | 0.44 | 2.20 |
| 7 | Labrafil M1944CS | Permeation Enhancer | 1.02 | 5.09 |
| 8 | Montelukast Sodium | Active | 3.3 | 16.48 |
| 9 | Sodium metabisulfite | Stabilizer | 0.84 | 4.19 |
| 10 | Propylparaben | Anti-microbial agent | 0.11 | 0.55 |
| 11 | Yellow #10 | Color | 0.28 | 1.40 |
| Total | | | 100.00 | 100.00 |

Preparation of a film product typically involves casting or otherwise thinly spreading the liquid film formulation on a substrate, drying (e.g., evaporating) all or most of the solvent(s) from the film to produce a thin, solid film sheet of material, and cutting the solid film sheet into individual unit dosage forms.

Figure 5:
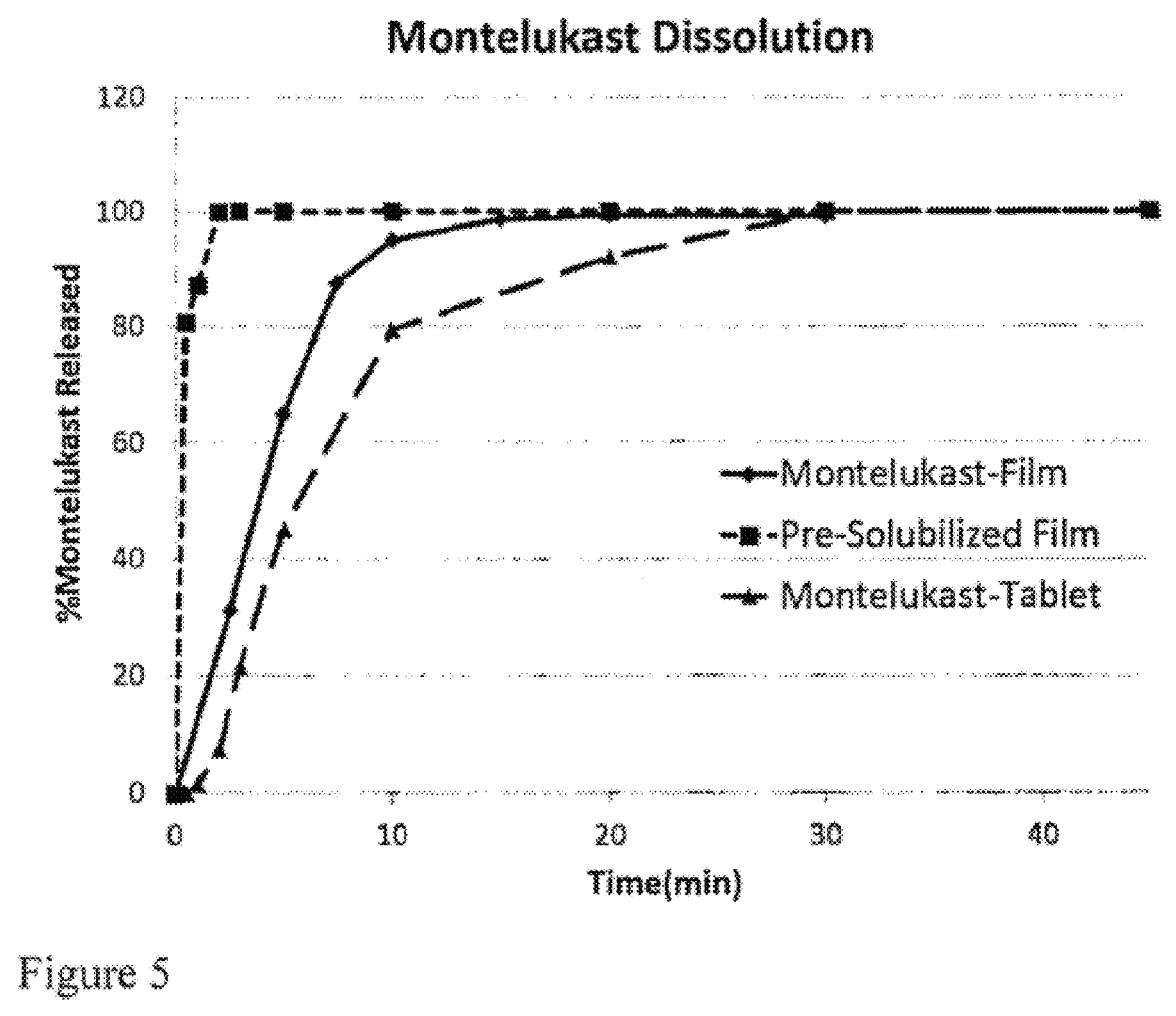

FIG. 5 shows an increased rate of dissolution of the present film oral dosage form of MTL when compared with the Singulair® MTL tablet. In addition, disclosed in FIG. 5 is the dissolution of the present film oral dosage form taking into account the buccal delivery method. In these experiments the "pre-dissolved film" refers to a film that is pretreated to simulates conditions typical of when the film is applied to oral mucosa of a human subject. Under such simulated conditions, the film slowly disintegrates before being subjected to the dissolution experiment. This method is used for a more representative comparison of the swallowed tablet behavior in the stomach with that of the swallowed film; the film is again much faster. In general, the dissolutions were conducted under the following conditions. The dosage consists of a 10 mg unit of either film or tablet. A USP dissolution apparatus was used to measure the API release profiles. Each dissolution container was filled with 900 mL of phosphate based simulated saliva buffer pH 6.8.

The paddle speed was set to 50 rpm and the temperature was kept at 37° C. Each pull point consisted of 8 mL and the time points were taken at 1, 2.5, 5, 7.5, 10, 15, 20, 30, 45. Samples were analyzed using UV absorption at 273 nm. Pre-solubilized Montelukast-Film dissolution was prepared by mixing a single film unit in 2 mL of simulated saliva buffer. This volume is considered to be representative of the volume of saliva generally found in the oral cavity under normal conditions. Data is summarized in Table 12.

TABLE 12

| Sample | Time to 80% API released (min.) |
|---|---|
| Montelukast-Films MTL03 & MTL10 | 6 |

TABLE 12-continued

| Sample | Time to 80% API released (min.) |
|---|---|
| Pre-dissolved Montelukast-Films | 1 |
| Montelukast-Tablet | 10 |

It was found that the MTL03 and MTL10-films reached 80% API released after approximately 6 minutes, while for the MTL-tablet to reach the same level of released API required 10 minutes. This highlights the rapid disintegration advantage of the film based platform. However, the most significant improvement using our film technology is observed when comparing the tablet to the pre-solubilized MTL03 and MTL10-films. This experiment is particularly interesting as it is a more representative comparison of how API is released from swallowed MTL-tablets versus swallowed MTL03 and MTL10-films in the comparable environmental conditions. Surprisingly, the pre-dissolved MTL03 and MTL10-films reaches 80% released API in only approximately 1 minute. This clearly demonstrates how the MTL03 and MTL10-films platform releases MTL significantly more quickly than the MTL-tablet dosage. This is believed to contribute towards the observed improved bioavailability during our Phase I Clinical study.

As demonstrated above, the oral film of MTL (principally MTL03) exhibits improved bioavailability compared to presently marketed products available as tablets/granules or suspensions. It is believed that the increased bioavailability of the MTL is related to the state of the MTL within the oral film. According to some embodiments, improved bioavailability of the oral film dosage form critically linked to the incorporation of solubilized MTL into the alkaline oral films, ensuring a rapid release of pre-solubilized therapeutic which is easily absorbed in the oral cavity and enterically. The alkalinity of the oral film as measured by the surface pH of the film favors dissolution of the MTL within the film. It is believed that the MTL remain soluble to some extend within the film due in part by the presence of residual solvent. Our preliminary results from manufacturing processes demonstrate the presence of between 5 to 9% dry w/w of residual solvent. As such, alkaline surface pH oral films of MTL (MTL01, MTL03, MTL05, MTL06 and MTL 07) are expected to exhibit the observed increased bioavailability of MTL03. The alkaline film layer is designed to keep MTL in a favorable solubilized condition that readily forms amorphous precipitates in the saliva upon oral administration of the film.

Illustrative, but non-limiting, examples of a formulation used to prepare a MTL oral films with EDTA are shown in Tables 13-20.

TABLE 13

| | | | MTL08 | |
|---|---|---|---|---|
| Item # | Description | Function | Composition (% wet w/w) | Composition % dry (w/w) |
| A | Methanol | Solvent (will be removed during manufacturing) | 0.28 | — |
| B | Purified Water | Solvent (will be removed during manufacturing) | 78.29 | — |
| 1 | Starch | Filler | 1.78 | 8.88 |
| 2 | HPC SL | Film former polymer | 8.22 | 41.04 |
| 3 | Xanthan gum | Thickener | 0.86 | 4.32 |
| 4 | Sucralose | Sweetener | 0.43 | 2.16 |
| 5 | Glycerol | Plasticizer | 1.82 | 9.07 |
| 6 | Montelukast Sodium | Active | 3.24 | 16.18 |
| 7 | Ascorbic acid | Stabilizer | 0.01 | 0.05 |
| 8 | Methylparaben | Anti-microbial agent | 0.11 | 0.54 |
| 9 | Titanium Dioxide | Opacifier | 0.27 | 1.32 |
| 10 | Yellow #10 | Color | 0.28 | 1.37 |
| 11 | HPC LF | Film former polymer | 0.72 | 3.58 |
| 12 | Calcium Carbonate | pH Modifier | 0.50 | 2.50 |
| 13 | Sodium glycocholate | Permeation Enhancer | 1.44 | 7.21 |
| | Disodium Edetate | Stabilizer | 0.36 | 1.78 |
| Total | | | 100 | 100.00 |

TABLE 14

| | | | MTL09 | |
|---|---|---|---|---|
| Item # | Description | Function | Composition (% wet w/w) | Composition % dry (w/w) |
| A | Methanol | Solvent (will be removed during manufacturing) | 0.2 | |
| B | Purified Water | Solvent (will be removed during manufacturing) | 79.68 | |
| 1 | Povidone | Film former polymer | 10.89 | 54.12 |
| 2 | Locust Bean Gum | Thickener | 0.86 | 4.30 |
| 3 | PEG 300 | Plasticizer | 0.15 | 0.73 |
| 4 | Labrafil M1944CS | Permeation Enhancer | 0.87 | 4.35 |
| 5 | Sucralose | Sweetener | 0.43 | 2.15 |
| 6 | Citric Acid | pH Modifier | 0.60 | 2.98 |
| 7 | Montelukast Sodium | Active | 3.24 | 16.12 |
| 8 | Disodium Edetate | Stabilizer | 0.36 | 1.78 |
| 9 | Propylparaben | Anti-microbial agent | 0.10 | 0.49 |
| 10 | Titanium Dioxide | Opacifier | 0.27 | 1.32 |

TABLE 14-continued

| | | | []MTL09 | |
|---|---|---|---|---|
| Item # | Description | Function | Composition (% wet w/w) | Composition % dry (w/w) |
| 11 | Yellow #10 | Color | 0.28 | 1.37 |
| 12 | HPC-GXF | Film former polymer | 2.07 | 10.31 |
| Total | | | 100.00 | 100.00 |

TABLE 15

| | | | ]MTL10 | |
|---|---|---|---|---|
| Item # | Description | Function | Composition (% wet (w/w) | Composition % dry (w/w) |
| A | Methanol | Solvent (will be removed during manufacturing) | 0.29 | — |
| B | Purified Water | Solvent (will be removed during manufacturing) | 79.68 | — |
| 1 | Starch | Filler | 1.78 | 8.88 |
| 2 | Pullulan | Film former polymer | 8.22 | 41.04 |
| 3 | Tara gum | Viscosity Modifier | 0.86 | 4.32 |
| 4 | PEG 300 | Plasticizer | 0.15 | 0.74 |
| 5 | Sorbitol P60W | Plasticizer | 1.80 | 8.97 |
| 6 | Sucralose | Sweetener | 0.43 | 2.16 |
| 7 | Glycerol | Plasticizer | 1.82 | 9.07 |
| 8 | Montelukast Sodium | Active | 3.24 | 16.18 |
| 9 | BHT | Stabilizer | 0.01 | 0.05 |
| 10 | Propylparaben | Anti-microbial agent | 0.11 | 0.54 |
| 11 | Titanium Dioxide | Opacifier | 0.27 | 1.32 |
| 12 | Yellow #10 | Color | 0.28 | 1.37 |
| 13 | HPC LF | Film former polymer | 0.72 | 3.58 |
| 14 | Disodium edetate | Stabilizer | 0.36 | 1.78 |
| Total | | | 100.00 | 100.00 |

TABLE 16

| | | | ]MTL11 | |
|---|---|---|---|---|
| Item # | Description | Function | Composition (% wet (w/w) | Composition % dry (w/w) |
| A | Methanol | Solvent (will be removed during manufacturing) | 0.29 | — |
| B | Purified Water | Solvent (will be removed during manufacturing) | 79.68 | — |
| 1 | Starch | Filler | 0.73 | 3.63 |
| 2 | PEO 200K | Film former polymer | 8.22 | 41.04 |
| 3 | PEO 100K | Film former polymer | 2.31 | 11.52 |
| 4 | Menthol | Flavor | 1.28 | 6.37 |
| 5 | Sorbitol P60W | Plasticizer | 1.65 | 8.24 |
| 6 | Sucralose | Sweetener | 0.43 | 2.16 |
| 7 | Citric Acid | pH Modifier | 0.44 | 2.21 |
| 8 | Montelukast Sodium | Active | 3.24 | 16.18 |
| 9 | Sodium Sulfite | Stabilizer | 0.01 | 0.05 |
| 10 | Methylparaben | Anti-microbial agent | 0.11 | 0.54 |
| 11 | Titanium Dioxide | Opacifier | 0.27 | 1.32 |
| 12 | Yellow #10 | Color | 0.28 | 1.37 |
| 13 | HPC JF | Film former polymer | 0.72 | 3.58 |
| 14 | Disodium Edetate | Stabilizer | 0.36 | 1.78 |
| Total | | | 100.00 | 100.00 |

TABLE 17

| | | | MTL12 | |
|---|---|---|---|---|
| Item # | Description | Function | Composition (% wet (w/w) | Composition % dry (w/w) |
| A | Methanol | Solvent (will be removed during manufacturing) | 0.29 | — |
| B | Purified Water | Solvent (will be removed during manufacturing) | 78.66 | — |
| 1 | Sodium Hydroxide | pH Modifier | 0.64 | 3.03 |
| 2 | HPMC E5 | Film former polymer | 3.15 | 14.98 |
| 3 | HPC-L | Film former polymer | 9.46 | 44.93 |
| 4 | PEG 300 | Plasticizer | 0.15 | 0.70 |
| 5 | Sorbitol P60W | Plasticizer | 1.80 | 8.54 |
| 6 | Sucralose | Sweetener | 0.43 | 2.05 |
| 7 | Sodium Metabisulfite | Stabilizer | 0.58 | 2.75 |
| 8 | Montelukast Sodium | Active | 3.24 | 15.40 |
| 9 | Disodium Edetate | Stabilizer | 0.38 | 1.83 |
| 10 | Propylparaben | Anti-microbial agent | 0.11 | 0.51 |
| 11 | Yellow #10 | Color | 0.28 | 1.31 |
| 12 | Oleic acid | Permeation Enhancer | 0.83 | 3.97 |
| Total | | | 100.00 | 100.00 |

25

TABLE 18

| | | | MTL13 | |
|---|---|---|---|---|
| Item # | Description | Function | Composition (% wet (w/w) | Composition % dry (w/w) |
| A | Methanol | Solvent (will be removed during manufacturing) | 0.29 | — |
| B | Purified Water | Solvent (will be removed during manufacturing) | 79.68 | — |
| 1 | Sodium Hydroxide | pH Modifier | 0.83 | 4.12 |
| 2 | Pullulan | Film former polymer | 9.17 | 45.80 |
| 3 | Xanthan gum | Thickener | 1.85 | 9.22 |
| 4 | PEG 300 | Plasticizer | 0.15 | 0.74 |
| 5 | Sodium sulfite | Stabilizer | 0.64 | 3.19 |
| 6 | Sucralose | Sweetener | 0.43 | 2.16 |
| 7 | Glycerol | Plasticizer | 1.82 | 9.07 |
| 8 | Montelukast Sodium | Active | 3.24 | 16.18 |
| 9 | Azone | Permeation Enhancer | 0.90 | 4.51 |
| 10 | Propylparaben | Anti-microbial agent | 0.11 | 0.54 |
| 11 | Titanium Dioxide | Opacifier | 0.27 | 1.32 |
| 12 | Yellow #10 | Color | 0.28 | 1.37 |
| 13 | Disodium Edetate | Stabilizer | 0.36 | 1.78 |
| Total | | | 100.00 | 100.00 |

TABLE 19

| | | | MTL14 | |
|---|---|---|---|---|
| Item # | Description | Function | Composition % wet (w/w) | Composition % dry (w/w) |
| A | Methanol | Solvent (will be removed during manufacturing) | 0.29 | — |
| B | Purified Water | Solvent (will be removed during manufacturing) | 79.68 | — |
| 1 | Ascorbic acid | Stabilizer | 0.95 | 4.76 |
| 2 | HPC-SL | Film former polymer | 9.49 | 47.37 |
| 3 | Xanthan gum | Thickener | 1.40 | 7.01 |
| 4 | PEG 300 | Plasticizer | 0.15 | 0.74 |

TABLE 19-continued

| | MTL14 | | | |
|---|---|---|---|---|
| Item # | Description | Function | Composition % wet (w/w) | Composition % dry (w/w) |
| 5 | Sorbitol P60W | Plasticizer | 1.80 | 8.97 |
| 6 | Sucralose | Sweetener | 0.43 | 2.16 |
| 7 | Labrafil M1944CS | Permeation Enhancer | 1.00 | 5.00 |
| 8 | Montelukast Sodium | Active | 3.24 | 16.18 |
| 9 | Sodium metabisulfite | Stabilizer | 0.83 | 4.12 |
| 10 | Propylparaben | Anti-microbial agent | 0.11 | 0.54 |
| 11 | Yellow #10 | Color | 0.28 | 1.37 |
| 12 | Disodium Edetate | Stabilizer | 0.36 | 1.78 |
| Total | | | 100.00 | 100.00 |

TABLE 20

| | ▯MTL15 | | | |
|---|---|---|---|---|
| Item # | Description | Function | Composition (% wet (w/w) | Composition % dry (w/w) |
| A | Methanol | Solvent (will be removed during manufacturing) | 0.27 | — |
| B | Purified Water | Solvent (will be removed during manufacturing) | 74.75 | — |
| 1 | Starch | Filler | 1.70 | 6.80 |
| 2 | Pullulan | Film former polymer | 7.85 | 31.43 |
| 3 | Tara gum | Viscosity Modifier | 0.83 | 3.30 |
| 4 | PEG 300 | Plasticizer | 0.14 | 0.56 |
| 5 | Sorbitol P60W | Plasticizer | 1.72 | 6.87 |
| 6 | Sucralose | Sweetener | 0.41 | 1.65 |
| 7 | Glycerol | Plasticizer | 1.74 | 6.95 |
| 8 | Montelukast Sodium | Active | 9.29 | 37.18 |
| 9 | BHT | Stabilizer | 0.01 | 0.04 |
| 10 | Propylparaben | Anti-microbial agent | 0.10 | 0.41 |
| 11 | Titanium Dioxide | Opacifier | 0.25 | 1.01 |
| 12 | Yellow #10 | Color | 0.26 | 1.05 |
| 13 | HPC LF | Film former polymer | 0.68 | 2.74 |
| Total | | | 100.00 | 100.00 |

The surface pH of each formulation was measured (Table 21).

TABLE 21

| Surface pH of MTL oral film | | |
|---|---|---|
| Formulation | Montelukast state | Surface pH |
| MTL01 | Solubilized | 8.51 |
| MTL02 | Precipitate | 5.23 |
| MTL03 | Solubilized | 8.80 |
| MTL04 | Precipitate | 6.73 |
| MTL05 | Solubilized | 10.44 |
| MTL06 | Solubilized | 11.42 |
| MTL07 | Partially solubilized | 7.38 |
| MTL08 | Solubilized | 8.25 |
| MTL09 | Precipitate | 4.98 |
| MTL10 | Solubilized | 8.52 |
| MTL11 | Precipitate | 5.81 |
| MTL12 | Solubilized | 10.26 |
| MTL13 | Solubilized | 11.26 |
| MTL14 | Partially solubilized | 7.14 |
| MTL15 | Solubilized | 8.98 |

Formulations MTL01, MTL03 MTL05 MTL06 MTL07 MTL08 MTL10 MTL12 MTL13, MTL14 and MTL15 are believed to be suitable for maintaining at least a portion of the MTL under a solubilized form within the film and improve the bioavailability of the Montelukast oral film when compared with Singulair® swallowable or chewable tablets. MTL02, MTL 03, MTL 09 and MTL11 are provide an undesired dosage form in which the Montelukast precipitates and hence does not provide the desired improved bioavailability derived from alkaline surface pH.

In certain embodiments of the MTL oral film it may be useful to increase the loading of API to generate higher in vivo concentrations and accumulation in serum and cerebral spinal fluid (CSF). It has been shown in the prior art that a regimen of MTL could leads to improved cognitive performance in people suffering from dementia, Alzheimer's, or other neurodegenerative disease. This improvement has been linked to MTL binding to leukotriene receptors in the brain and thereby reducing and mitigating any inflammatory response. Previous anecdotal studies have stated specific ranges of daily MTL ingestion to maintain constant blood levels, and have reported varying degrees of cognitive improvement. Despite some anecdotal evidence, there is a lack of understanding on the mechanism of action of montelukast and most method of treatment disclosed are not based on sound studies. Anecdotal evidence fails to teach the required amount of MTL for an effective treatment and thus challenge the required amount of MTL for cognitive improvement nor have they adequately evaluated any observed cognitive improvement using industry accepted test methods.

Disclosed herein are animals studies using Alzheimer's disease genetically modified mice which have been performed. In these experiments the mice are divided into three groups: (1) Negative Control (no MTL), (2) 1 mg daily dosing, (3) 3 mg daily dosing. The mice behavioral improvement has been monitored using two animal based cognitive measuring tests. Following the duration of the study the mice are sacrificed and analyzed for MTL accumulation in serum and CSF. This new study has demonstrated surprising data that shows a strong correlation between cognitive improvement in genetically modified Alzheimer's mice and increasing MTL dosage strength. The experimental design, results and data interpretation is discussed in the following paragraphs.

This disclosure compares pharmacokinetics of Montelukast-gel and Montelukast-Versafilm™ (formulation MTL15) in adult mice and test the efficacy of the leukotriene receptor antagonist Montelukast (Montelukast-Versafilm) in two different concentrations compared to placebo in a mouse model of AD. The first disclosed experiment is the Mouse—Pharmacokinetics Comparison of Montelukast-Versafilm to Montelukast Gel Single Dosing. The disclosure outlined in this experiment to determine the PK of Montelukast-Versafilm compared to Montelukast in methylcellulose-gel in mice.

The Material and Methods used to compare MTL15 with MTL in Methyl cellulose-gel.

20≥three month old female C57B16 mice (from Charles river) were singularly treated with two different doses of Montelukast either in form of a methylcellulose gel or in form of a VersaFilm (Table 22). After one and three hours blood samples were taken from the vena saphena of each mouse. After seven hours mice were euthanized with a mix of Ketamin (273 mg/kg), Xylazin (71 mg/kg) und Acepromazin (4 mg/kg). Blood samples were taken by cardiac puncture and CSF samples were taken trough the cisterna *magna*. The study was approved by the BMBWF Austria (number: BMBWF-66.019/0019-V/3b/2018). Serum was collected and analyzed with LC-MS/MS.

| Group | N | Treatment |
|-------|---|-----------|
| 1 | 5 | Gel low dose |
| 2 | 5 | Gel high dose |
| 3 | 5 | Film low dose |
| 4 | 5 | Film high dose |

Test item (Montelukast-Versafilm) came in form of an adhesive buccal film. Films used for the animal study were in sheets with 1 mg/cm$^2$ Montelukast, sheets with 3 mg/cm$^2$ Montelukast (MTL15), and sheets of placebo. In pre-experiments, we found that a circular punch of 7 mm$^2$ (exactly 7,065 mm$^2$)(3 mm diameter punches using a hole pliers) is well received by the mice. The 7 mm$^2$ punched pieces were prepared before administration. The use of 3 mm diameter punches of Montelukast-Versafilm sheets was based on the following assumptions and previous data. A) 10 mg/kg/day of Montelukast through an oral gavage in wt and in alpha-syn overexpressing mice achieved a pharmacoexposure of approx. 600 ng/ml in serum and 1/50 (12 ng/ml) in CSF (Marschallinger and Aigner, unbuplished data). 10 mg/kg/day in adult rats achieved approximately 200 ng/ml in serum and approx. 5 ng/ml in CSF, similar to a 10 mg/day dose in a human (Marschallinger et al., 2015). Our conclusion on that was that a 10 mg/kg/day in mice is a three times overdose compared to the approved dose of 10 mg/day in humans. Therefore, to achieve a 10 mg/day human—equivalent dose, we tried to reach approximately the range of 3.3 mg/kg/day in the present AD mouse experiment for the low dose (group B) and 10 mg/kg/day in the high dose (group C). B) We initially assumed that our cohort of mice have an approximate weight of 20 g. The use of the 7 mm$^2$ punches of 1 mg/cm$^2$ Montelukast-Versafilm in a 20 g mouse would relate to 3.5 mg/kg/day dose, the 3 mg/cm$^2$ punch would relate to a 10.5 mg/kg/day dose, which would be in the desired range.

Mice used in the pharmaco-exposure experiment were 12 weeks old and had a mean bodyweight of 20-21 g (according to FIG. 7), meaning the 7 mm$^2$ punches of the respective films were in the desired range.

Serum and CSF was prepared as described in Marschallinger et al., 2015.

The LC-MS/MS method for the quantification of montelukast in serum was described earlier (Muppavarapu, R., et al., 2014) with a modified sample preparation as used in Challa, et al., 2010. Briefly, sample preparation consisted of a simple protein precipitation protocol. Therefore, 12.5 μL 100% FA were added to 50 μL of serum or CSF, vortexed briefly before the addition of 150 μL 100% ACN containing MTL-d6 as internal standard. After vortexing for two minutes, all samples were centrifuged at 10 500×g for 10 minutes at 4 C. For serum samples, 20 μL of the clear supernatant were added to 40 μL of mobile phase A (1 mM ammonium formate in water containing 0.1% FA). The supernatants (180 μL) of CSF extraction were dried under a constant nitrogen flow at 45° C. Completely dried samples were reconstituted with 60 μL 1 mM ammonium formate in 25/75 (vol/vol) acetonitrile/water containing 0.1% FA.

Chromatographic separation was carried out on an Agilent 1200 series quaternary HPLC system using a Chromolith Performance RP18-e column (100×3 mm) from Merck operated a temperature of 45° C. with 1 mM ammonium formate in water containing 0.1% FA as mobile phase A and 1 mM ammonium formate in 95/5 (vol/vol) acetonitrile/water containing 0.1% FA as mobile phase B. Gradient elution at a flow rate of 0.5 mL/min started from 25.0% to 95.0% B in 10.0 min, followed by a flushing step with 95.0% B for 0.8 min followed by an re-equilibration step with 25.0% B for 3.2 min. Total time for a single chromatographic run was 14.0 min. Injection volumes of 20 μL for serum and 30 μL for CSF samples were chosen.

Selected reaction monitoring (SRM) measurements for MTL as well as for the d6-internal standard in obtained samples were performed on an API 4000 LC-MS/MS triple quadrupole system in positive ionization mode. The quantifier ion transitions of MS/MS detection were m/z 586.20568.2 for MTL and m/z 592.217574.4 for MTL-d6. Calibration curves were derived from ratios of the peak areas of MTL and the internal standard using 1/D-weighted linear least-squares regression of the area ratio versus the concentration of the corresponding internal standard MTL-d6. Analyst software 1.6.2 was used for detection, analysis and quantification of data.

Figure 7:
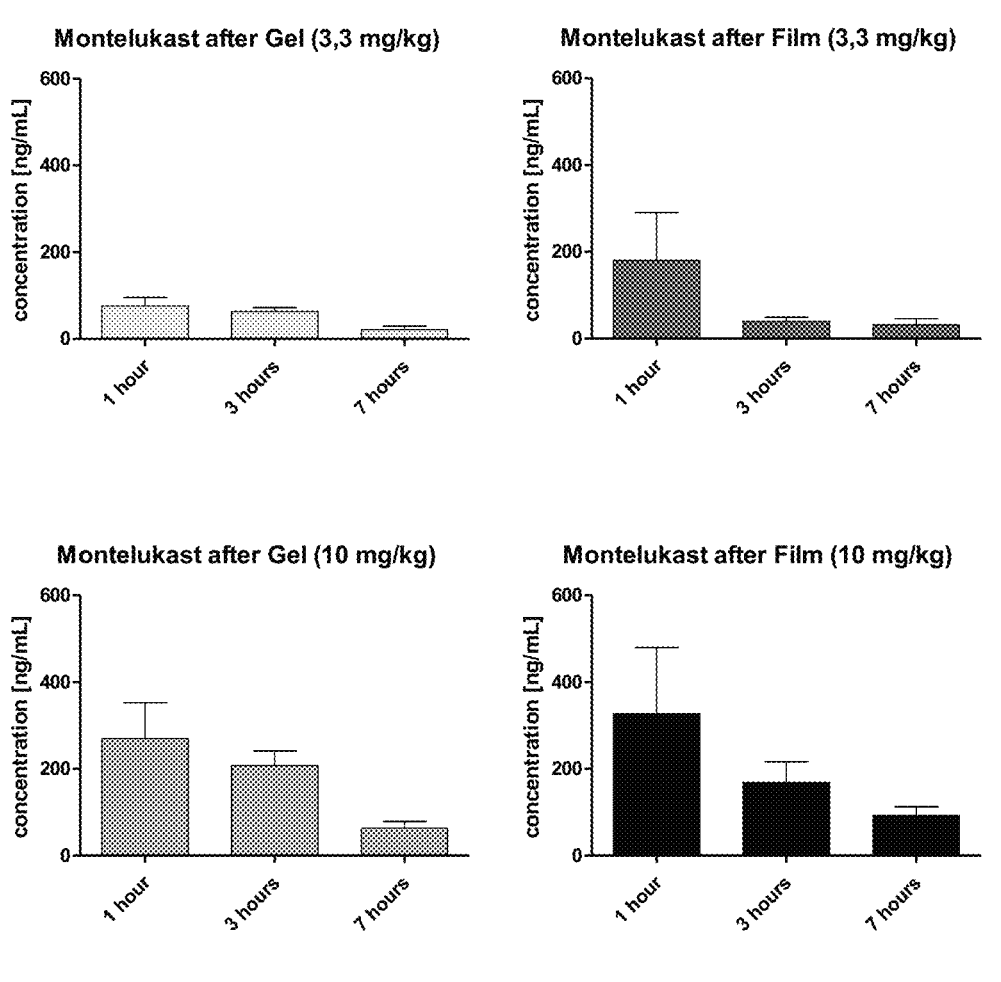
FIG. 7 is a graphical comparison of gel versus film in low dose and high dose of MTL (data are presented as mean+ SEM).
Figure 8:
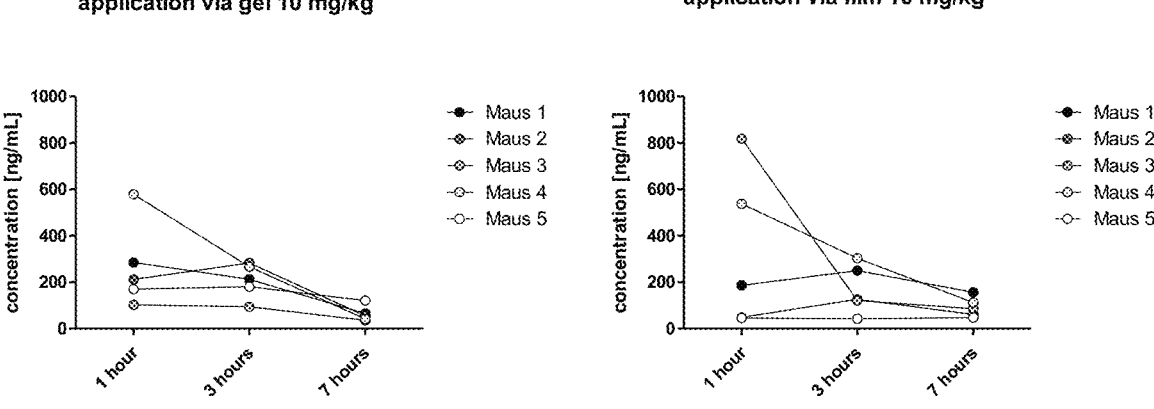
FIG. 8 is a graphical representation of individual response to MTL treatment in the high dose groups.
Figure 9:
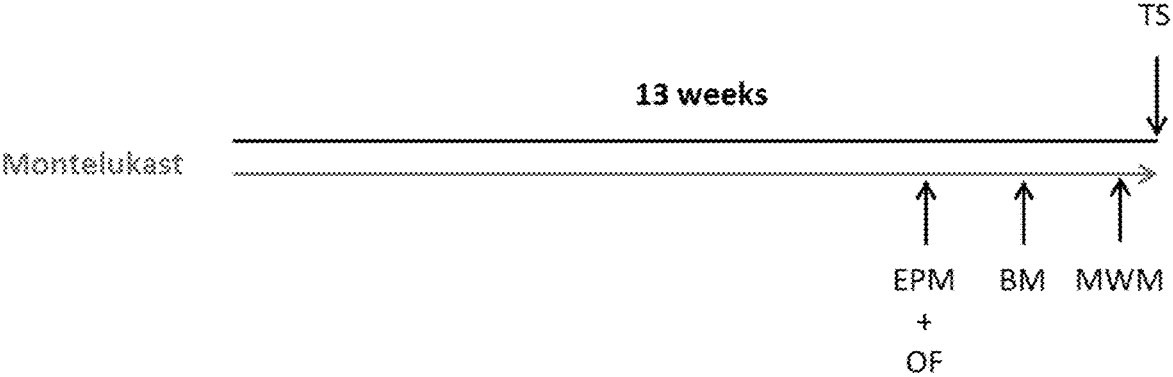
FIG. 9 is a timeline of an in vivo study.

Referring now to FIGS. 7 and 8, the results shows a similar time dependent decrease of MTL concentration in the serum in gel and film. The date suggests a potential peak for MTL in serum reaches the Cmax within the first hour. But after 1 hour the concentration decreases within seven hours. Furthermore, in gel as well as in film the MTL concentration is higher after the high dose than after the administration of the low dose. This confirms a dose-response scalability, and demonstrates that a higher loading of MTL can achieve higher blood concentrations as needed to achieve effective therapeutic serum concentrations. Individual analysis of the animals from the high dose treatment groups showed a variation in initial MTL intake for both application methods. Due to very low volumes of CSF from the mice an analysis for MTL concentration did not show a measurable result. These results unexpectedly confirm significantly higher bioavailability obtained using the oral film dosage form over the gel. This improved performance is linked to the selection of mucoadhesive polymers to keep the film in close contact to the mucosa and the amorphous solubilized MTL locked into the film matrix, both which contribute to improved uptake of MTL.

Efficacy of Montelukast-Versafilm in the 5×FAD Animal Model of Alzheimer's Disease As disclosed herein this study tested the efficacy of two different doses (approx. 3.3 mg/kg/day, approx. 10 mg/kg/day) of Montelukast (Montelukast-Versafilm) in improving cognition in the 5×FAD mouse model of Alzheimer's disease.

Study Design

Animals: 45 five month old 5×FAD mice (roughly between 20 and 30 g of weight, females were in general lighter than males, see data) expressing five mutations related to AD (APP KM670/671NL (Swedish), APP I716V (Florida), APP V717I (London), PSEN1 M146L (A>C), PSEN1 L286V) were used.

Medication and Treatment: The Test item (Montelukast-Versafilm) came in form of an adhesive buccal film. Oral films sheets with 1 mg/cm$^2$ Montelukast, sheets with 3 mg/cm$^2$ Montelukast, and sheets of placebo we made for this study. In pre-experiments, we found that a circular punch of 7 mm$^2$ (3 mm diameter punches using a hole pliers) is well received by the mice. The 7 mm$^2$ punched pieces were prepared daily before administration.

Outcome parameters: Effects on behavior were assessed through the behavioral tests Open Field (OF), Barnes Maze (BM), Morris Water Maze (MWM) and Elevated Plus Maze (EPM).

Mice were allocated to three groups as described in the table below.

TABLE 23

| Treatment group allocation | | |
|---|---|---|
| Group | Treatment | N |
| A (5 × FAD tg) | Placebo | 15 |
| B (5 × FAD tg) | Low dose (3, 3 mg/kg) | 15 |
| C (5 × FAD tg) | High dose (10 mg/kg) | 15 |

Animals were treated daily with Montelukast film or placebo for 3 weeks. Behavioral tests started in week 11.

TABLE 24

| | | | | | | | | | | | | | | | | | | | | | |
|---|---|---|---|---|---|---|---|---|---|---|---|---|---|---|---|---|---|---|---|---|---|
| | | | | | | | | | | | time plan of behavioral tests | | | | | | | | | | |
| | | | | | | | | | | | Week | | | | | | | | | | |
| | 1-10 | | | | | 11 | | | | | | 12 | | | | | | 13 | | | | |
| | | | | | | | | | | | Day | | | | | | | | | | |
| | | 1 | 2 | 3 | 4 | 5 | 6 | 7 | 1 | 2 | 3 | 4 | 5 | 6 | 7 | 1 | 2 | 3 | 4 | 5 | |
| Treatment | X | X | X | X | X | X | X | X | X | X | X | X | X | X | X | X | X | X | X | X | |
| OF | | | | | | X | | | | | | | | | | | | | | | |
| MWM | | | | | | | | | | | | | | | | | X | X | X | X | X |
| EPM | | | | | X | | | | | | | | | | | | | | | | |
| BM | | | | | | | | | X | X | X | X | X | | | | | | | | |
| TS | | | | | | | | | | | | | | | | | | | | | X |

The study was conducted in accordance with the study plan (see Table 24) and QPS standard operating procedures. QPS is a fully Association for Assessment and Accreditation of Laboratory Animal Care (AAALAC) accredited facility. All procedures in this study complied with the Animal Care and Welfare Committee. Animals were maintained according to the animal welfare regulations of the Ministry of Science of the Austrian government (TVG 2012 in the appropriate valid version). The study was approved by the styrian provincial government number ABT13-14688/2018-4. The least number of animals was used in compliance with current regulations and scientific integrity. The welfare of the animals was taken into account in terms of number and extent of procedures to be performed. The health status of each individual animal was evaluated prior to starting the study. Only animals in apparently good health condition were included.

Housing

Animals were housed in individual ventilated cages on standardized rodent bedding. The room temperature was stable at approximately 24° C. and the relative humidity was maintained between 40 to 70%. Animals were housed under a constant light-cycle (12 hours light/dark; light from 6 am to 6 pm). Dried, pelleted standard rodent food (Altromin) as well as normal tap water was available ad libitum.

Identification

Animals were numbered consecutively by classical ear punching. Each cage was identified by a colored card indicating the study number, sex, the individual registration numbers (IRN) of the animals, date of birth, as well as the group allocation. The genotype of each animal was determined by PCR specific for the transgenic construct. Each mouse was genotyped using DNA isolated from tail tips prior to study start.

Group Allocation

Only animals in apparently good health condition were included in the study. Allocation of animals to treatment groups was done per cage and in a way that the animal age was evenly balanced across all groups. Animals were enclosed in two starting groups (cohorts) comprising animals of all treatment groups. The number of animals in a starting group was limited to ensure same age and uniform handling.

Health Status and Cage-Side Observations

Before starting the experimental in vivo phase, the health status of each individual animal was evaluated. During the study, any notable cage-side observations were recorded and immediately reported to the attending veterinarian to decide on further actions (e.g. euthanasia). Animals were observed once daily for mortality, abnormalities, and signs of pain and distress. Findings were recorded as they are observed. Body weights and health status were recorded weekly. In case of premature deaths (1 case) or unscheduled euthanasia, a necropsy was performed.

Premature Termination

Individual animals that showed signs of chronic pain or distress or any of the following clinical symptoms were euthanized: Anorexia/weight loss (a chronic body weight loss of more than 20%), hunched posture, lethargy or persistent recumbency, rough hair coat, dyspnea, diarrhea, high grade of dehydration, circling or head tilt, limb paralysis, progressive dermatitis, jaundice or anemia, bleeding from any orifice, self-induced trauma, cachexia, any condition interfering with eating or drinking (e.g. difficulty with ambulation), excessive or prolonged hyperthermia or hypothermia.

In case of an abnormally high death rate or other side effects that might have been attributable to the treatment, treatment of animals would have been discontinued until the cause of side effects was clarified. This was not the case in this study.

Behavioral Tests

EPM: The EPM is at present one of the most widely used tests to study anxiety in small rodents. This test is based on the aversion of rodents to open spaces and height. The EPM apparatus is elevated from the floor. The equipment is a four arm maze with two opposing open arms and two opposing closed arms, raised 50 cm above ground. The test is conducted under red light illumination. On test day, animals are brought into the experimental room 45-60 min prior to testing for acclimatization. A mouse is placed in the center area facing the open arm. The behavior during the test session is recorded for five minutes, and behavioral parameters are calculated, such as time spent in the open and in the closed arms, number of visits in the open and closed arms as well as latency to enter the open arm. Data is generated by using Noldus Ethovision XT.

OF: In this test, a Plexiglas Open Field (48×48 cm; TSE-System®) is used. Infrared photo beams are placed in a 1.4 cm distance around the box. To detect rearing (standing on the hind paws) another row of photo beams are mounted 4 cm above the first one. Each test session lasts for 20 minutes to check the mice's behavior in the new surroundings. Thereafter the number of fecal boli is counted, as a measure of emotionality. The Open Field is cleaned with 70% ethanol after each mouse to eliminate odor traces. Testing is performed under standard room lighting conditions during the light phase of the circadian cycle. Mice must are brought to the testing room 45-60 minutes to habituate to the standard testing room conditions.

BM: The maze consists of a circular platform (92 cm diameter) with 20 equally spaced holes (5 cm diameter; 7.5 cm between holes) along the perimeter and is elevated 105 cm above ground. In the Barnes Maze, animals receive reinforcement to escape from the open platform surface to a small dark recessed chamber, a "target box", located under the platform. Mice can access the target box through the target hole. From the center of the maze, all holes look identical and the target box is not visually discriminated. Visual 3D cues are placed surrounding the maze. For quantification, a computerized video tracking system (Noldus Observer) is used. Four trials on each of four consecutive days are performed. A single trial lasts for a maximum of 120 seconds and stops earlier, if the mouse enters the target. If the mouse does not find the target box within this time, the experimenter guides the mouse to the target. Mice are allowed to rest there for 10-15 seconds.

24 hours after the last trial on day 4, mice are tested in the probe trial (PT). During the PT, the target hole is closed and the number of visits as well as the abidance in the target quadrant is recorded. For quantification of escape latency (time [sec] to find the target hole), of pathway (length of the trajectory [meter] to reach the target), of target zone crossings and of the abidance in the target quadrant in the PT), a computerized video tracking system (Noldus Ethovison) is used.

MWM: Spatial learning capacities of all animals were tested in the Morris Water Maze (MWM). The MWM is performed using the following pattern: Four trials on each of four consecutive days are performed. In all trials, the platform is located in the northeast (NE) quadrant of the pool and mice start from predefined positions (southeast (SE), southwest (SW), northwest (NW)). A single trial lasted for a maximum of 60 seconds. In case the mouse did not find the hidden, diaphanous platform within this time, the mouse was guided to the target. Mice were allowed to rest on the platform for 10-15 sec to orientate in the surrounding.

24 hours after the last trial on day 4, mice were tested in the probe trial (PT). During the PT, the platform was removed from the pool and the number of crossings over the former target position as well as the abidance in the target quadrant were recorded. For the quantification of escape latency (the time [sec] to find the hidden platform), of pathway (the length of the trajectory [meter] to reach the target), of target zone crossings and of the abidance in the target quadrant in the PT), a computerized video tracking system (Biobserve, Viewer III) was used.

Figure 22:
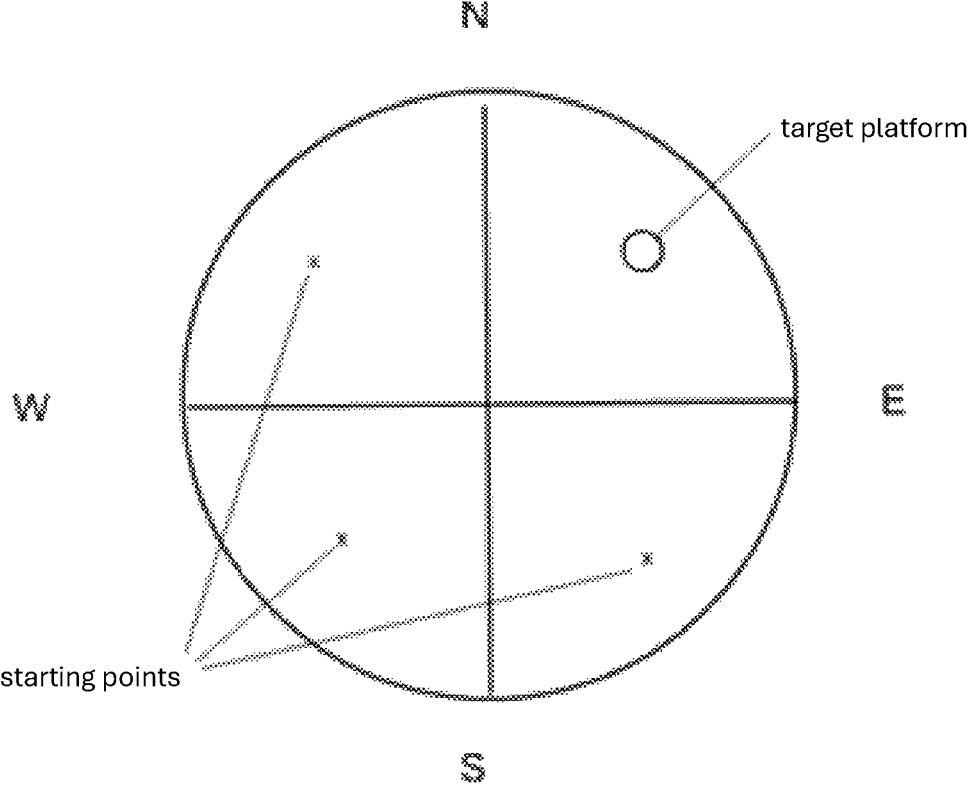
FIG. 22 is a schematic of exemplary start positions in the different trials.

The start positions in the different trials were e.g. shown in FIG. 22:

| Tissue sampling | | | | | | |
|---|---|---|---|---|---|---|
| Trial 1 | Trial 2 | Trial 3 | Trial 4 | PT | Platform | |
| Day 1 | SW | SE | NW | SW | — | NE |
| Day 2 | NW | SE | SW | NW | — | NE |
| Day 3 | SW | NW | SE | SW | — | NE |
| Day 4 | SE | SW | NW | SE | — | NE |
| Day 5 | — | — | — | — | SW | NE |

All animals were euthanized after the behavioral tests in week 13 by Pentobarbital injection (600 mg/kg). Eyes, blood, CSF, brain and spleen were collected from all animals. Blood was collected by cardiac puncture. Serum was collected and was snap frozen on dry ice and stored at −80° C.

After deep anesthesia, mice were transcardially perfused with 0.9% saline and the brains were taken out and hemisected. Right hemibrains were fixed by immersion in freshly prepared 4% paraformaldehyde/PB (pH=7.4) for 48 hours at 4° C. Thereafter, right hemibrains were transferred to 30% sucrose in PBS solution for 24-72 hours at 4° C. to ensure cryoprotection. Right hemibrains were transferred a second time to fresh 30% sterile filtered sucrose in PBS solution and stored at 4° C. until sent to Institute of Molecular Regenerative Medicine, PMU, in Salzburg. The left hemisphere was dissected into Hippocampus, Cortex and rest, weighed and snap frozen on dry ice in distinct tubes and stored at −80° C. Spleens were fixed by immersion in freshly prepared 4% paraformaldehyde/PB for 48 hours at 4° C. and subsequently stored in 30% sucrose. Eyes were fixed by immersion in freshly prepared 4% paraformaldehyde/PB for 2 hours, before transferred to PBS for 48-72 hours. Eyes were transferred a second time into 15% sterile filtered sucrose in PBS solution and stored at 4° C.

Safety

Figure 10:
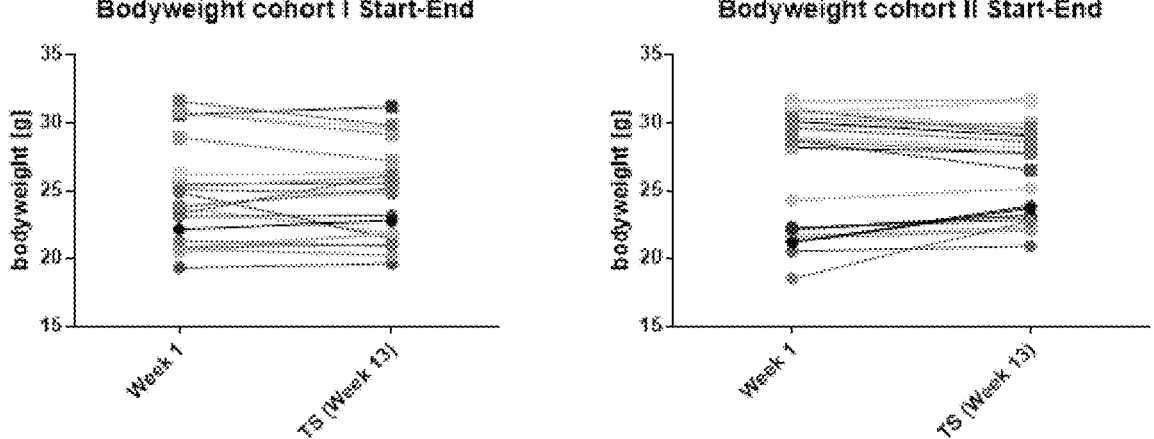
FIG. 10 is a graphical representation of body weights from week 1 and week 13 (bodyweights were recorded weekly, but for reasons of presentation only start and end points are displayed in this graph).

We did not observe any adverse effects of daily Montelukast treatment. Mice from both cohorts displayed stable bodyweight (FIG. 10) and health status during the whole experiment, regardless of the treatment. In general, and independent of the treatment, female mice were lighter compared to the male mice (21.9+/−SD g in females, 28.8+/−SD g in males at the beginning of the treatment). One animal from group B died unexpectedly as a result of an epileptic seizure, which was not related to the treatment, but most likely to the genetic background of the mouse.

Determination of Montelukast Dose and Pharmacoexposure

The use of 3 mm diameter (exactly 7,065 mm$^2$ big) punches of Montelukast-Versafilm sheets was based on the following assumptions and previous data. A) 10 mg/kg/day of Montelukast through an oral gavage in wild type (wt) and in alpha-syn overexpressing mice achieved a pharmacoexposure of approx. 600 ng/ml in serum and 1/50 (12 ng/ml) in CSF. 10 mg/kg/day in adult rats achieved approximately 200 ng/ml in serum and approx. 5 ng/ml in CSF, similar to a 10 mg/day dose in a human (Marschallinger et al., 2015). Our conclusion was that a 10 mg/kg/day in mice is a three times overdose compared to the approved dose of 10 mg/day in humans. Therefore, to achieve a 10 mg/day human-equivalent dose, we tried to reach approximately the range of 3.3 mg/kg/day in the present AD mouse experiment for the low dose (group B) and 10 mg/kg/day in the high dose (group C). B) We initially assumed that our cohort of mice have an approximate weight of 20 g. The use of the 7 mm$^2$ punches of 1 mg/cm$^2$ Montelukast-Versafilm in a 20 g mouse would relate to 3.5 mg/kg/day dose, the 3 mg/cm$^2$ punch would relate to a 10.5 mg/kg/day dose, which would be in the desired range.

Comparing that with the real data (see FIG. 2), we are in the range of approx. 20 to 30 g of mouse weight. Therefore, mice were treated with the following Montelukast concentrations:

Group B (low dose): 7 mm$^2$ of 1 mg/cm$^2$ is equivalent to 0.07 mg/30 g-20 g: 2.3-3.5 mg/kg/day, in average 2.9 mg/kg/day. Nevertheless, in the results, we refer to the pre-assumed dose of 3.3 mg/kg.

Group C (high dose): in average 8.7 mg/kg/day, referred to in here as 10 mg/kg

Figure 11:
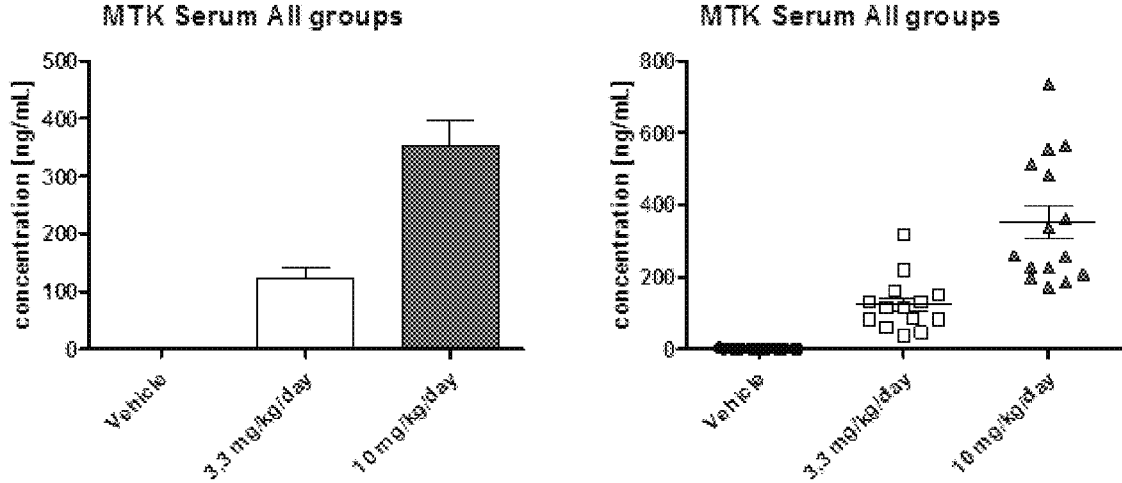
FIG. 11 is a graphical representation of pharmacological analysis of serum samples for MTL concentration.
Figure 12:
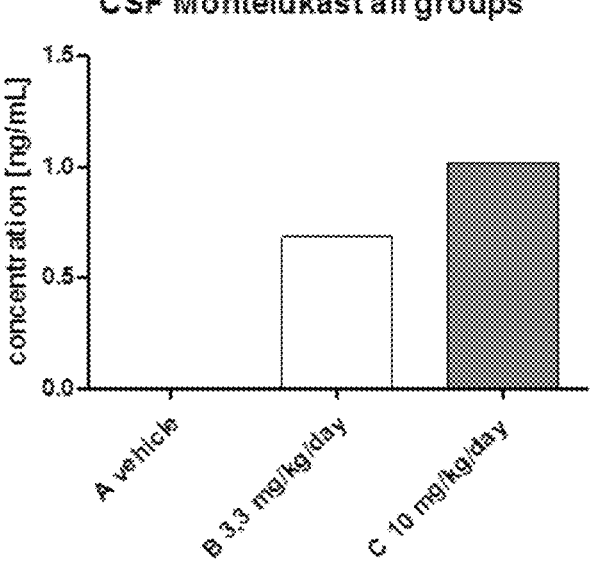
FIG. 12 is a graphical representation of pharmacological analysis of pooled CSF samples for MTL concentration.

The 3 months treatment of 5×FAD mice with placebo and with low and high dose of Montelukast-Versafilm resulted in the following exposure at approximately 7 hours after the last treatment:

Due to the low amount of CSF from the individual mice CSF samples were pooled within the treatment groups to obtain measurable amounts for each group. The analysis showed no MTL in serum or CSF samples of the untreated group (FIGS. 11 and 12). In both treatment groups MTL was detected in serum and CSF samples. Surprisingly, the high dose treatment group had approximately 3 times more MTL in the serum (FIG. 11) and 1,5 times more MTL in the CSF (FIG. 12) compared to the low dose treatment group. This unexpected evidence supports our previous observation of dose-scalability, furthermore it indicates that dose-scalability also occurs in the CSF, and leads to increased MTL accumulation in the CSF which is critical for MTL to generate its desired therapeutic effect.

Behavioural Analysis

Figure 13:
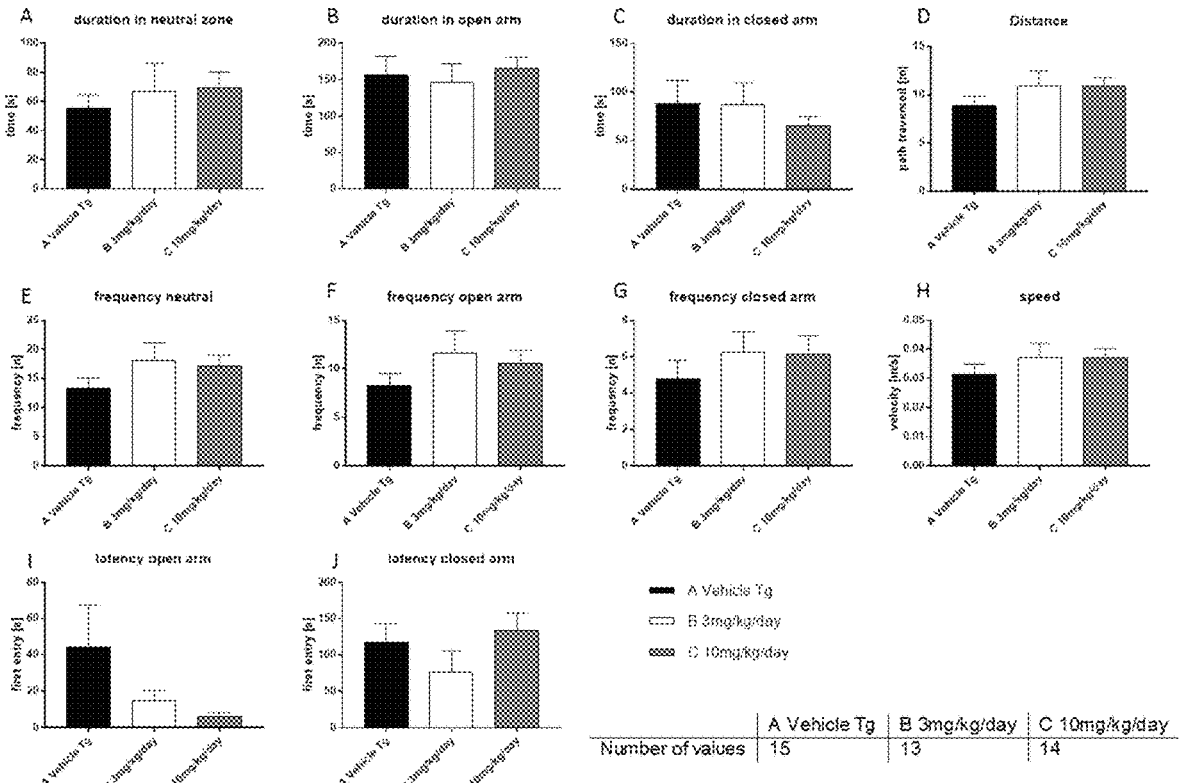
FIG. 13 is a graphical representation of grouped analysis of 44 mice in the EPM (data are presented as mean+SEM, data were tested for significant effects using one way anova and Kruskal-Wallis-Test).
Figure 14:
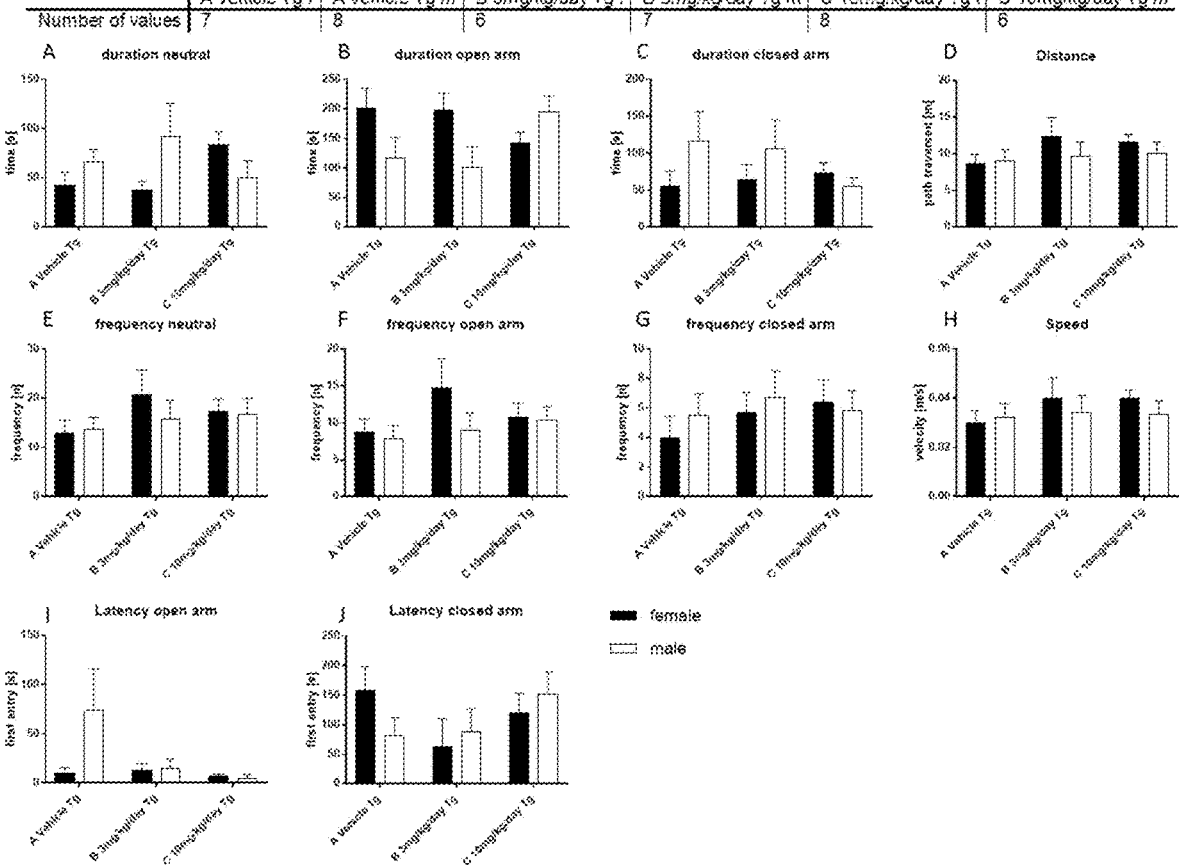
FIG. 14 is a graphical representation of gendered analysis of 44 mice in the EPM (data are presented as mean+SEM, data were tested for significant effects with two way anova).

Animals of all groups have behaved similarly in the Elevated Plus Maze (EPM) (FIG. 13). Still it seems that mice treated with the high dose of MTL spent less time in the closed arm (FIG. 13 C). Furthermore there was a trend for treated mice to cover a longer distance (FIG. 13 D) with a higher velocity (FIG. 13 H) compared to placebo treated mice. In general, treated mice showed more explorative behavior, as shown by the higher frequencies to change arms (FIG. 13 E-G). The gendered analysis did not reveal significant differences between male and female mice for any parameter (FIG. 14), nor significant differences between the groups for males and females.

The Open Field test was performed on day five of week 11. This test was used to measure the spontaneous activity of the animals. The measured parameters were activity (speed of movement=5-20 cm/s), hyperactivity (speed of movement >20 cm/s), rearing behavior (number), traversed distance (m) and time spent in the middle and the border of the box (as an indicator of thigmotaxis). First, data of the entire test period (20 min) was evaluated and is presented below. In a second step the test period was divided into 4 intervals (5 minutes each) and these were analyzed with regard to the above mentioned parameters to look for changes in behavior over time.

Figure 15:
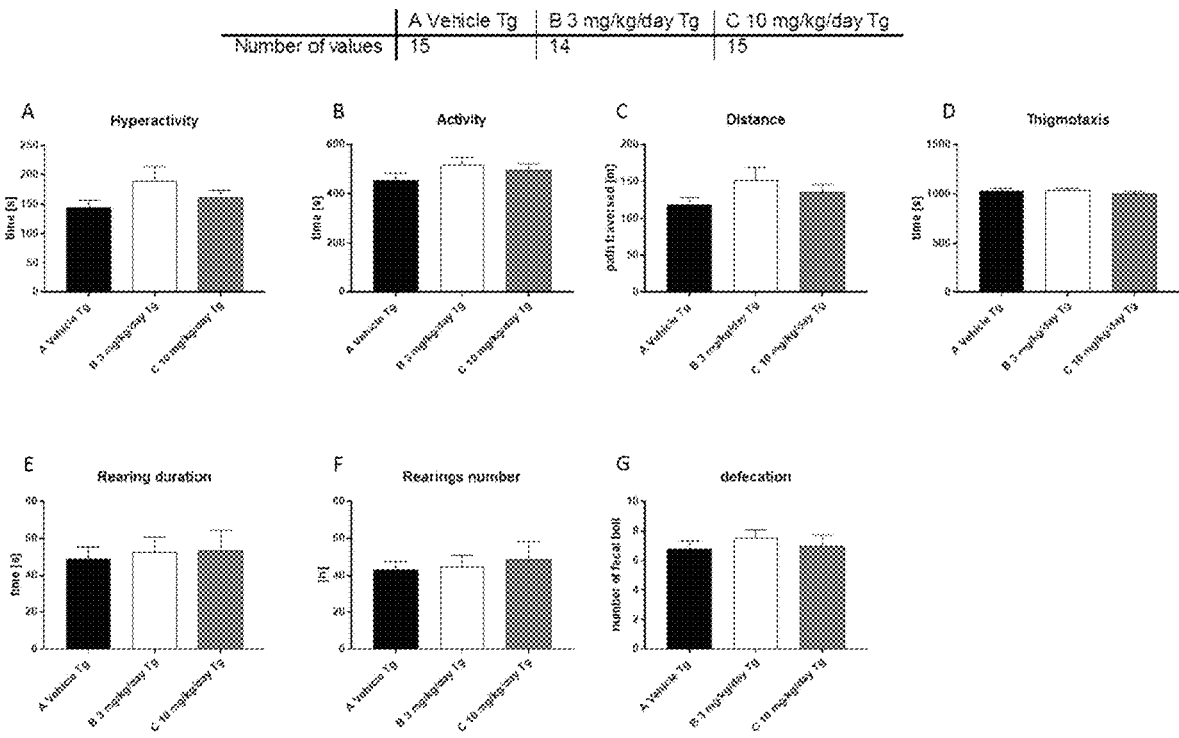
FIG. 15 is a graphical representation of grouped analysis of behavioral data from OF 20 minutes (data are presented as mean+SEM, data were tested for significant differences with one way anova or Kruskal-Wallis-Test).
Figure 16:
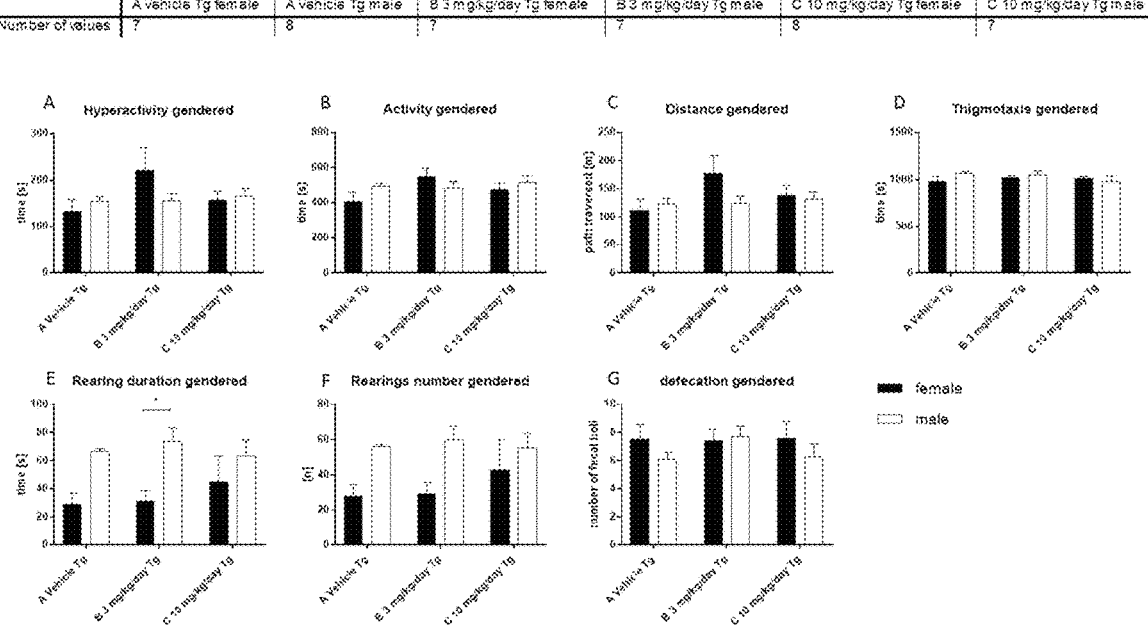
FIG. 16 is a graphical representation of gendered analysis of behavioral data from OF 20 minutes (data are presented as mean+SEM, data were tested for significant differences with two).

The grouped analysis (FIG. 15) for the entire test period revealed normal and similar behavior for animals of all groups. No significant differences between groups were found in any parameter. The gendered analysis revealed a significant difference in the rearing duration (FIG. 16 E) between male and female mice treated with the low dose of MTL. Also there was a significant difference between placebo treated female mice and female mice treated with the low dose of MTL in the parameter of hyperactivity.

The analysis of 5 minute intervals revealed a significant increase over time for group A (vehicle) and group B (low dose MTL) in the parameter of activity and for group B also in the parameter of hyperactivity and distance. Mice from group C (high dose MTL) did not increase their level of activity over time. Mice from all three groups did show a similar increase in rearing number and duration as well as a constant level of thigmotaxis. There was no significant difference between groups for any parameter in any interval (data shown in ppt RD51600—Open Field 5 minutes).

Barnes Maze

Figure 17:
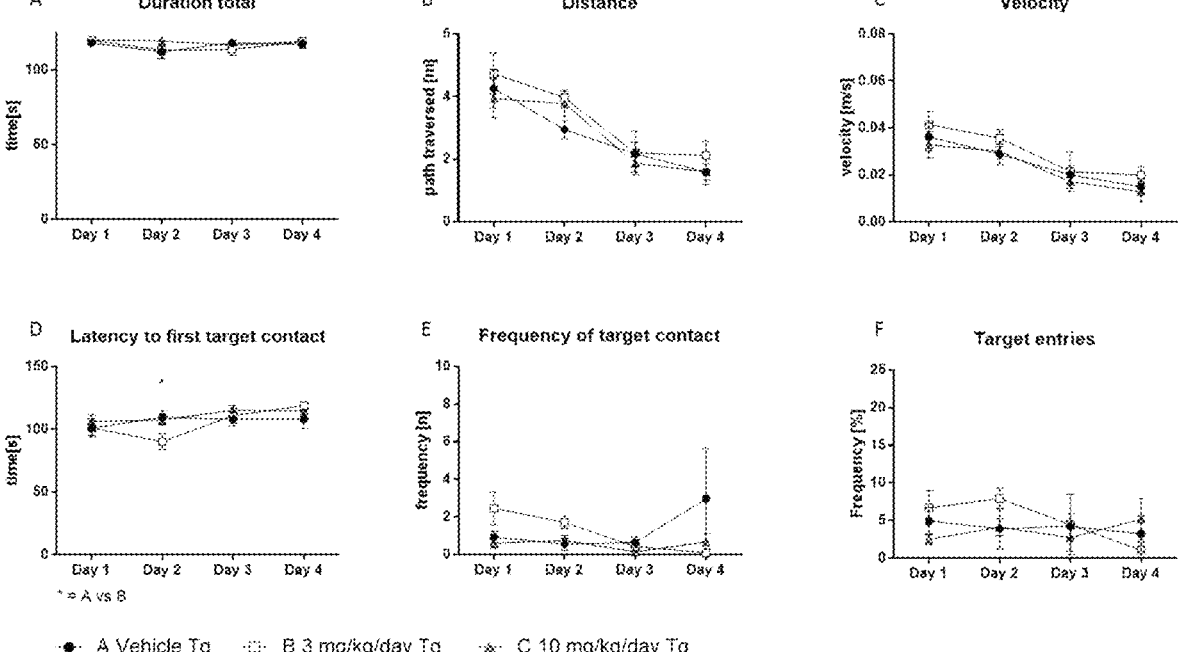
FIG. 17 is a graphical representation of Cohort I data (presented as mean+SEM, statistics were made using repeated measures two way anova).

5×FAD mice of an age similar to mice of our cohorts were previously positively tested in the Barnes Maze at QPS. The test clearly showed that the mice, although they have learning deficits in this test compared to wild-type mice, were performing the task, meaning that they were searching for the target. Much to our surprise, 5×FAD mice of the first cohort did not perform the test at all, meaning that they were not moving after placing them onto the arena. This is illustrated in FIG. 17 A. The decrease in distance and velocity was caused by increasing immobility of the mice instead of learning behavior. In the PT 90% of the mice did not perform. After intense discussion with the staff at QPS, we concluded that the "non-performing" in the test could be due to the fact that the mice were handled daily for 11 weeks and therefore used to being out of their home cage. As a consequence of the handling they were not stressed enough by the surrounding conditions to be motivated to hide themselves. Based on this observation the test conditions were adjusted for the second cohort.

Figure 18:
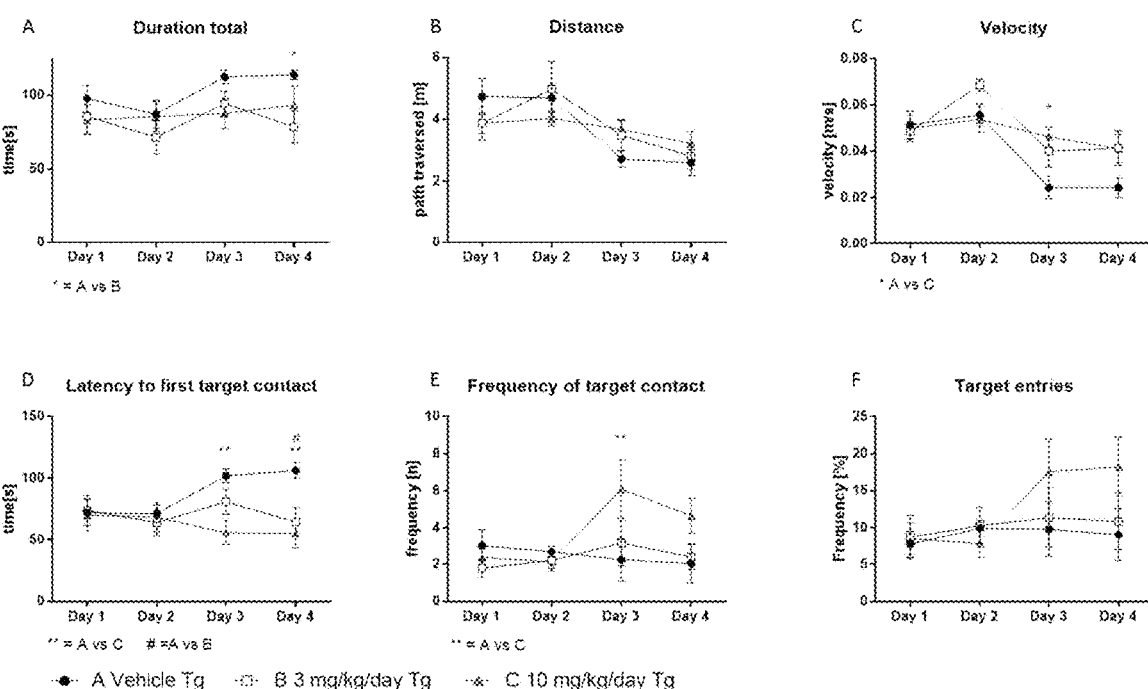
FIG. 18 is a graphical representation of Cohort II data (presented as mean+SEM, statistics were made using repeated measures two way anova).

A sound cue was added (80 db "white noise") to increase the mice motivation to leave the platform. The sound started with beginning of recording and ended as soon as the mouse entered the target hole. In the second cohort placebo treated mice did show a comparable behavior to mice from cohort I, meaning an increase in immobility with time, which caused the decrease in the parameters distance and velocity (FIGS. 18 B and C). Placebo treated mice did not show learning behavior as determined by the increase in the parameters of duration total and latency to first target contact (FIGS. 18 A and E). However, unexpectedly mice from cohort II, treated with Montelukast did show learning behavior compared to placebo (FIG. 18). Mice treated with the high dose of Montelukast learned faster than mice treated with low dose, as determined by the lower latency to first target contact, which was significantly lower in group C than in group A on day 3 and 4 and also significantly lower in group B compared to group A in day 4, the higher frequency of target contact, which was significantly higher in group C than in group A on day 3, and the higher frequency of target entries (meaning the mouse completely entered the target whole and stopped the experiment), which was not significant, but a trend can be seen. Decrease in distance and velocity were not caused by immobility in treated mice (FIGS. 18 B and C). The increase in the total duration can be explained by the fact that it took the mice longer to completely enter the target hole with time. Still, the latency to first target contact (meaning the mice ran to the target hole and put their head inside) decreased over time. In the PT some mice of the second cohort also did not perform the test, probably because they were used to the surrounding conditions by then (personal communication with QPS).

Morris Water Maze

Figure 19:
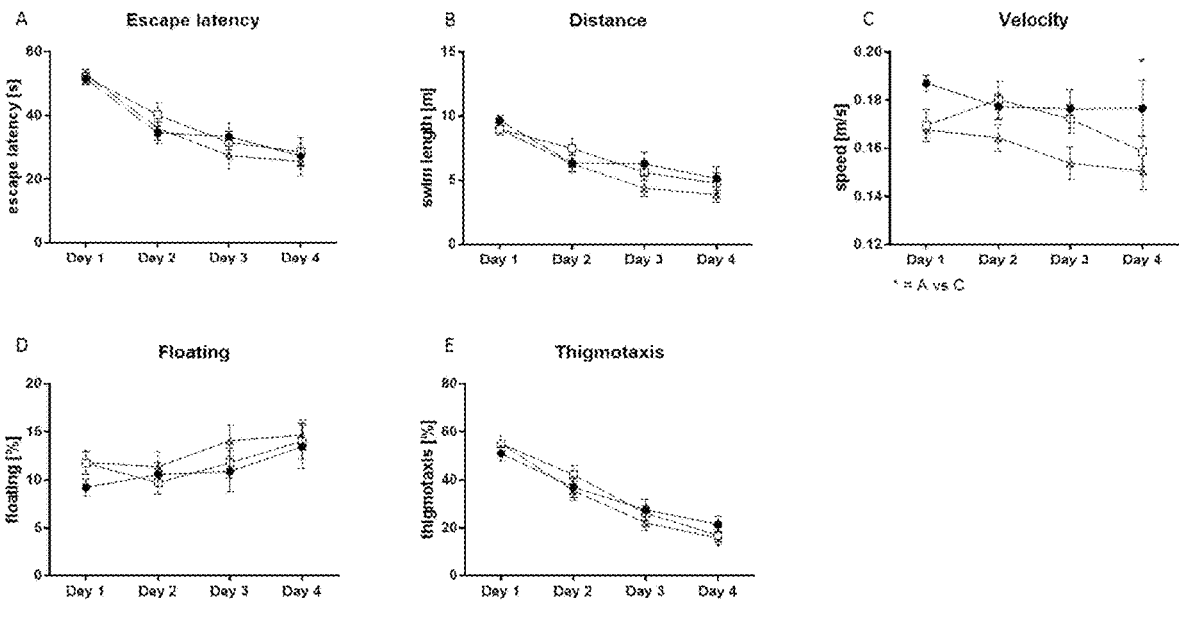
FIG. 19 is a graphical representation of grouped analysis of MWM data (presented as mean+SEM, statistics were made using repeated measures two way anova).
Figure 20:
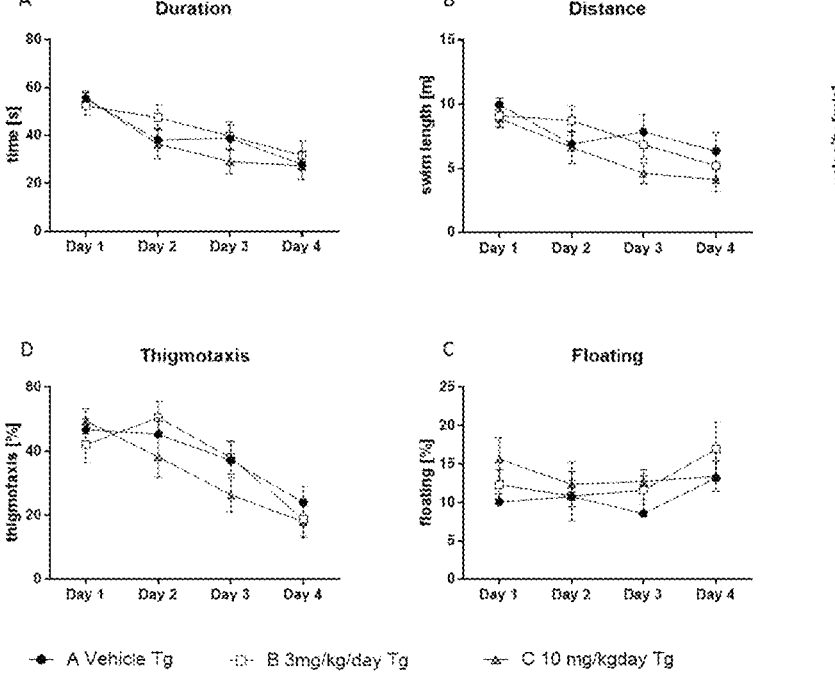
FIG. 20 is a graphical representation of analysis of long term memory (data are presented as mean+SEM, statistics were made using repeated measures two way anova).

Results of the grouped analysis indicate that mice treated with the high dose of MTL performed better in the MWM. They show a trend to better learning, as shown by shorter escape latencies on day 3 and 4 (FIG. 19 A), shorter distances (FIG. 19 B) and slightly less thigmotaxis (FIG. 19 E). However, with the dosage used the differences are not significant for these parameters. Still, mice treated with the high dose of MTL did show reduced speed compared to placebo treated mice, which was significant on day 4 (FIG. 19 C). In a separate analysis only values of the first trial each day were used for every animal to look specifically at long term memory (FIG. 20). In this analysis the trend to better learning of the high dose treatment group is also seen suggesting better long term memory after high dose MTL treatment.

Figure 21:
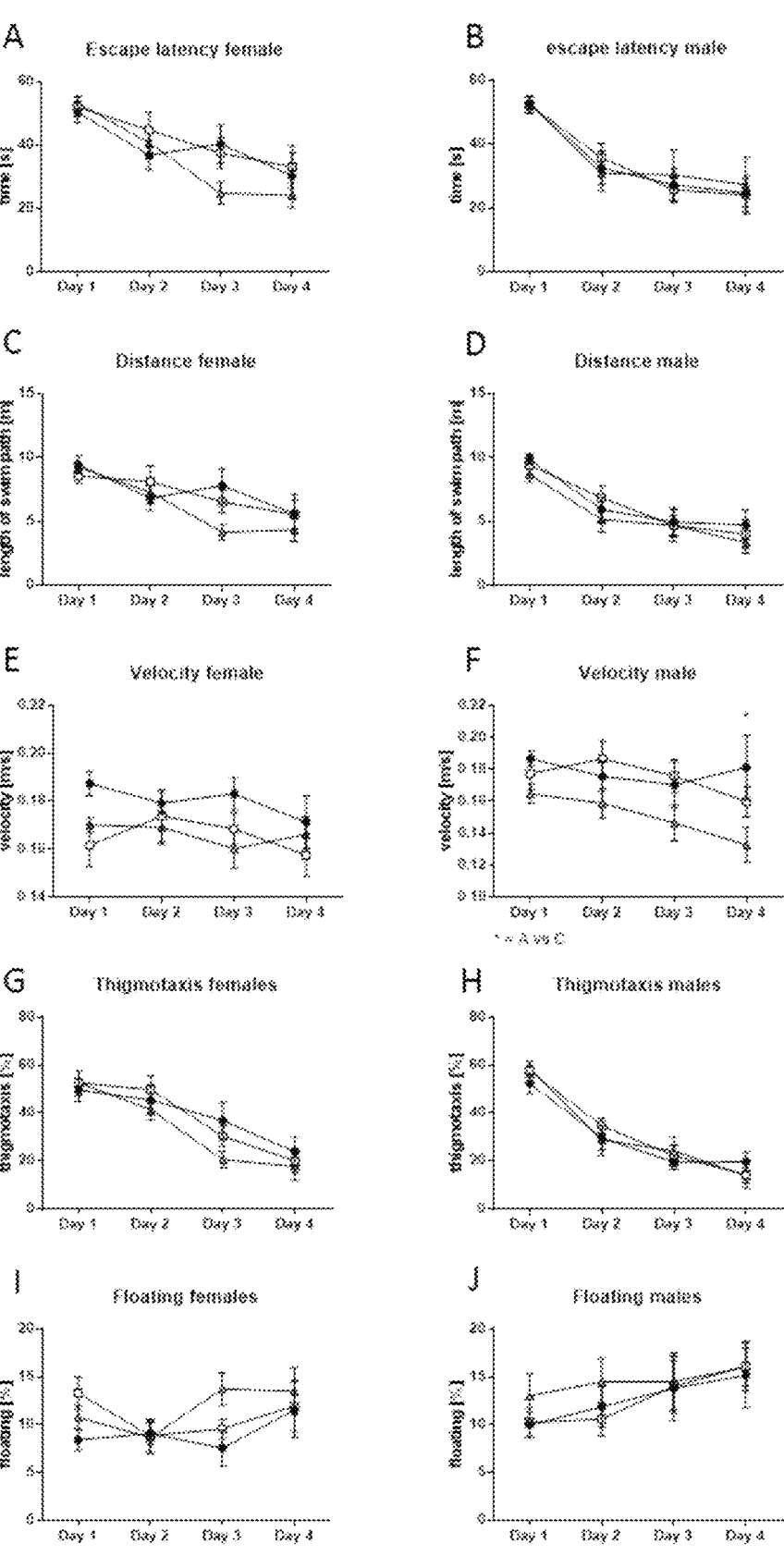
FIG. 21 is a graphical representation of gendered analysis (data are presented as mean+SEM, statistics were made using repeated measures two way anova).

The gendered analysis showed that significantly reduced speed was more common among the males than the females. A comparison between sexes revealed a general trend that males performed slightly better than females in the MWM trough all groups, but except from the significantly lower speed, there were no significant differences between groups for females and males (FIG. 21).

Additional to the overall grouped and gendered analysis both cohorts were analysed separately for differences between the groups due to the different conditions in the prior test (Barnes Maze). Indeed the results differed between both. In cohort I mice treated with the high dose of MTL showed less learning behavior than the placebo treated animals, as determined by the parameters escape latency and thigmotaxis. Mice from group C performed better than mice treated with the low dose of MTL and placebo treated mice. This noticeable difference in escape latency was not seen in the PT, which was due to three animals of the high dose treatment group that did not cross the target zone at all. In cohort II treated mice showed escape latencies that were comparable to wild type on day 3 and 4 and also placebo treated mice showed escape latencies comparable to untreated 5×FAD mice from other studies (personal communication with QPS).

LC-MS/MS analysis showed that MTL reaches the blood and to a smaller amount also the brain. This was unexpectedly found to be dose dependent. The previous pharmacoexposure experiment revealed that in the blood MTL concentration shows an early peak and subsequently decreases within several hours. Interestingly after long lasting daily treatment the concentration of MTL in the blood after seven hours was higher (~300-400 ng/mL) than seven hours after a singular administration of MTL (~100-150 ng/mL). This indicates there is some accumulation of MTL after a long term treatment with MTL. This is very significant as it allows administration of MTL on a daily basis for high doses 30 mg/day in human which is expected to show increased therapeutic effect in AD subject population.

According to embodiments, it is disclosed a method of treating or at least partially alleviating the effects of AD in patient by administering a dose of MTL of between 20 to 75 mg per day for a prolonged period of at least 30 to 90 subsequent days, preferably at least 60 to 90 days.

In general and independent of dosage, treatment did not negatively affect mice during the study. In the tests for anxiety and general activity all mice performed well and there was no significant effect of MTL compared to vehicle. This study thus demonstrated that an elevated amount of MTL may be administered over a prolonged period of time, thereby promoting any dose dependent therapeutic effect without the occurrence of safety issues.

Most surprisingly, in tests for learning and memory the analysis revealed significant effects of MTL treatment on latency to first target contact, on frequency of target contact in the BM and on velocity in BM and MWM. Also some trends towards an effect of MTL on cognition can be seen, for example better learning behavior and less thigmotaxis in the MWM. Furthermore the results of the EPM, suggesting less anxiety (less time spent in closed arm, more time spent in open arm) and more explorative behavior (frequency) of the high dose treatment group compared to placebo treated animals, as well as the significantly reduced speed in the MWM (C vs A) indicate a possible effect of MTL treatment on emotional levels. In an early case study where MTL was given off-label to patients with dementia, some patients and caregivers, reported beneficial effects of MTL on agitation and anxiety (Rozin et al., 2017).

Lastly, the fact that, in this study treatment effects on behavior as well as trends are mostly seen between animals from the high dose treatment group compared to the placebo treated group, shows that with a higher range of dosing the differences would probably be more pronounced.

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. A method of treating neuroinflammation comprising administering to a patient in need thereof an oral film dosage form having an alkaline surface pH from about 7.5 to about 9.5 and containing about 10 to about 50 mg of Montelukast maintained in an amorphous form in a polymer matrix, the oral film dosage form being administered once or twice daily to provide release of up to 80% of the Montelukast in about 2 minutes to about 6 minutes of up to a total dose of 75 mg of Montelukast per day for the treatment of neuroinflammation, and repeating administration once or twice daily for a continuous period of at least 60 days.

2. The method of claim 1, wherein the oral film dosage form is administered for a period of at least 90 days.

3. The method of claim 1, wherein the oral film dosage form has a surface pH from about 8 to about 9.5.

4. The method of claim 1, wherein the oral film dosage form has a surface pH from about 8.5 to about 9.5.

5. The method of claim 1, wherein the oral film dosage form has a surface pH from about 9 to about 9.5.

6. The method of claim 1, wherein the oral film dosage form comprises between 20 and 50 mg of Montelukast.

7. The method of claim 1, wherein the oral film dosage form comprises between 30 and 50 mg of Montelukast.

8. The method of claim 1, wherein the oral film dosage form is unbuffered.

9. The method of claim 1, wherein Montelukast is solubilized in the oral film dosage form.

10. The method of claim 1, wherein the release of Montelukast provides an AUC (area under the curve) form about 3120 ng·h/mL to about 4700 ng·h/mL.

11. The method of claim 1, wherein the release of Montelukast provides an Cmax form about 475 ng/ml to about 720 ng/ml.

12. A method of treating neuroinflammation comprising:

administering to a patient in need thereof an oral film dosage form having an alkaline surface pH from about 7.5 to about 9.5 and containing about 10 to about 50 mg of Montelukast maintained in the oral film dosage form in an amorphous form, the oral film dosage form providing precipitation of Montelukast upon contact with saliva to provide a Montelukast suspension; the oral film dosage form being administered once or twice daily to provide up to a total dose of 75 mg of Montelukast per day for the treatment of neuroinflammation, and repeating administration once or twice daily for a continuous period of at least 60 days.

13. The method of claim 12, wherein the oral film dosage form is administered for a period of at least 90 days.

14. The method of claim 12, wherein the oral film dosage form has a surface pH from about 8 to about 9.5.

15. The method of claim 12, wherein the oral film dosage form has a surface pH from about 8.5 to about 9.5.

16. The method of claim 12, wherein the oral film dosage form has a surface pH from about 9 to about 9.5.

17. The method of claim 12, wherein the oral film dosage form comprises between 20 and 50 mg of Montelukast.

18. The method of claim 12, wherein the oral film dosage form comprises between 30 and 50 mg of Montelukast.

19. The method of claim 12, wherein the oral film dosage form is unbuffered.

* * * * *